US010618881B2

(12) United States Patent
Park et al.

(10) Patent No.: US 10,618,881 B2
(45) Date of Patent: Apr. 14, 2020

(54) METHODS OF FORMING AROMATIC CONTAINING COMPOUNDS

(71) Applicant: REGENTS OF THE UNIVERSITY OF MINNESOTA, Minneapolis, MN (US)

(72) Inventors: Dae Sung Park, Minneapolis, MN (US); Christoph Krumm, Minneapolis, MN (US); Maura Koehle, Leland, NC (US); Kristeen Joseph, Minneapolis, MN (US); Dionisos G. Vlachos, Voorhees, NJ (US); Raul F. Lobo, Newark, DE (US); Paul J. Dauenhauer, Sunderland, MA (US)

(73) Assignees: Regents of the University of Minnesota, Minneapolis, MN (US); University of Delaware, Newark, DE (US)

( * ) Notice: Subject to any disclaimer, the term of this patent is extended or adjusted under 35 U.S.C. 154(b) by 0 days.

(21) Appl. No.: 15/773,992

(22) PCT Filed: Nov. 7, 2016

(86) PCT No.: PCT/US2016/060774
§ 371 (c)(1),
(2) Date: May 4, 2018

(87) PCT Pub. No.: WO2017/079718
PCT Pub. Date: May 11, 2017

(65) Prior Publication Data
US 2018/0327376 A1 Nov. 15, 2018

Related U.S. Application Data

(60) Provisional application No. 62/252,200, filed on Nov. 6, 2015.

(51) Int. Cl.
*C07D 307/46* (2006.01)
*C07D 307/36* (2006.01)
*C07D 307/58* (2006.01)
*C07D 307/64* (2006.01)

(52) U.S. Cl.
CPC ......... *C07D 307/46* (2013.01); *C07D 307/36* (2013.01); *C07D 307/58* (2013.01); *C07D 307/64* (2013.01)

(58) Field of Classification Search
CPC .. C07D 307/46; C07D 307/36; C07D 307/58; C07D 307/64
See application file for complete search history.

(56) References Cited

U.S. PATENT DOCUMENTS 2,411,567 A   11/1946  Fisher
4,233,333 A   11/1980  Trummlitz
4,308,215 A   12/1981  Vaughan
4,477,382 A   10/1984  Goel
6,187,981 B1   2/2001  Marinangeli
2011/0071056 A1   3/2011  Saini
2015/0150768 A1   6/2015  West
2018/0327375 A1  11/2018  Krumm
2018/0327376 A1  11/2018  Park

FOREIGN PATENT DOCUMENTS

| EP | 0245835 A2 | 11/1987 |
| EP | 0268820 A2 | 6/1988 |
| WO | WO 2005051936 A1 | 6/2005 |
| WO | WO 2015084813 A1 | 6/2015 |
| WO | WO 2016028845 A1 | 2/2016 |
| WO | WO 2017079718 A1 | 5/2017 |
| WO | WO 2017079719 A1 | 5/2017 |

OTHER PUBLICATIONS

Reddy et al., 54 Catalysis Letts. 95-100 (1998) (Year: 1998).*
Bel'skii & Shulkin, 32(6) Russ. Chem. Rev. 307-321 (1963) (Year: 1963).*
Scully & Brown, 19(6) J. Org. Chem. 894-901 (1954) (Year: 1954).*
Cheng & Huber, 14 Green Chem. 3114-3125 (2012) (Year: 2012).*
Mukaiyama, 28 Org. Reactions, Chap. 3, The Directed Aldol Reaction, p. 203-331 (1982) (Year: 1982).*
Scholz et al, 10 Liebigs Ann. Chem. 1935-1950 (1985) (Year: 1985).*
International Patent Application No. PCT/US16/60774), filed Nov. 7, 2016; International Search Report / Written Opinion dated Apr. 6, 2017; 21 pages.
International Patent Application No. PCT/US16/60774, filed Nov. 7, 2016; International Preliminary Report on Patentability dated May 17, 2018; 12 pages.
International Patent Application No. PCT/US16/60775, filed Nov. 7, 2016; International Search Report / Written Opinion dated Apr. 25, 2017; 32 pages.
International Patent Application No. PCT/US16/60775, filed Nov. 7, 2016; International Preliminary Report on Patentability dated May 17, 2018; 17 pages.
Abid, "Application of the Phase Transfer Catalysis to the Synthesis of New Furanic Polyesters" Jan. 2005 *Journal de la Societe Chimique de tunisie*: 1-9.
Adamkeiwicz, "α-Regioselective Aqueous Mukaiyama Aldol Reaction of 2- (Trimethylsilyloxy)furan with Pyruvates: α-Regioselective Aqueous Mukaiyama Aldol Reaction of 2-(Trimethylsilyloxy)furan with Pyruvates" Oct. 2016 *European Journal of Organic Chemistry*, 5 pages.
ASTM D2281-10. Standard test method for evaluation of wetting agents by the skein test; ASTM International, West Conshohocken, PA, 2010. Online: https://www.astm.org/Standards/D2281.htm (Accessed Oct. 9, 2018). DOI: 10.1520/D2281-10, www.astm.org.
Augustin, "Nano- and micro-structured assemblies for encapsulation of food ingredients" Apr. 2009 *Chem. Soc. Rev.*, 38(4):902-912.
Bajpai, "Laundry Detergents: An Overview" 2007 *J. Oleo Sci*, 56:327-340.

(Continued)

*Primary Examiner* — Timothy R Rozof
(74) *Attorney, Agent, or Firm* — Mueting, Raasch & Gebhardt, P.A.

(57) ABSTRACT

Methods that include acylating an aromatic containing compound by reacting the aromatic containing compound with an anhydride containing compound to form an acylated aromatic containing compound.

20 Claims, 6 Drawing Sheets

(56) References Cited

OTHER PUBLICATIONS

Bardach, "Detergents: Effects on the chemical senses of the fish *Ictalurus natalis* (le Sueur)" Jun. 1965 *Science*, 148:1605-1607.

Biermann, "Oils and Fats as Renewable Raw Materials in Chemistry" Apr. 2011 *Angew. Chem., Int. Ed.*, 50:3854-3871.

Boethling, "Designing small molecules for biodegradability" Jun. 2007 *Chem. Rev.*, 107:2207 -2227.

Briggs, "Quality of rivers of the United States, 1975 water year; based on the National Stream Quality Accounting Network (NASQAN); US Geological Survey," 1977. (pdf in two parts).

Cao, "Alkylation of benzene with dodecene. The activity and selectivity of zeolite type catalysts as a function of the porous structure" Aug. 1999 *Appl. Catal. A*, 184:231-238.

Ceresana (Market Intelligence. Consulting.) Online: http://www.ceresana.com/en/market-studies/chemicals/surfactants/ceresana-market-study-surfactants.html. Accessed Oct. 9, 2018. 3 pages.

Chang, "Ultra-selective cycloaddition of dimethylfuran for renewable p-xylene with H-BEA" 2014 *Green Chem.*, 16:585-588.

Chao, "11C(4)-alkyl substituted furanyl cyclobutenediones as potent, orally bioavailable CXCR2 and CXCR1 receptor antagonists 11" Jul. 2007 Bioorganic & Medicinal Chemistry Letters, Pergamon, Amsterdam, NL, 17(13):3778-3783.

Clayden, Organic Chemistry $2^{nd}$ Ed., *Electrophilic aromatic substitution*, Oxford, New York, 2012, pp. 493-494, cover page, title page and table of contents.

Corma, "Delaminated zeolites: Combining the benefits of zeolites and mesoporous materials for catalytic uses" 1999 *J. Catal.*, 186:57-63.

Corma, Chemical routes for the transformation of biomass into chemicals Jun. 2007 *Chem. Rev.*, 107:2411-2502.

Faba, "Aqueous-phase furfural-acetone aldol condensation over basic mixed oxides" 2012 *Appl. Catal. B*, 113-114:201-211.

Faba, "Performance of bifunctional Pd/MxNyO (M=Mg, Ca; N=Zr, Al) catalysts for aldolization-hydrogenation of furfural-acetone mixtures" 2011 *Catal. Today*, 164(1):451-456.

Falbe, *Surfactants in Consumer Products*; Springer-Verlag: Heidelberg Germany, 1987. Cover page, title page and table of contents.

Fendler, "Polymerized surfactant vesicles: Novel membrane mimetic systems" Mar. 1984 *Science*, 223:888-894.

Gassama, "Sulfonated surfactants obtained from furfural" 2013 *Green Chem.*, 15:1558-1566.

Green, "Diels—Alder cycloaddition of 2-methylfuran and ethylene for renewable toluene" 2015 *Appl. Catal. B*, 180:487-496.

Guo, "Highly active and recyclable Sn-MWW zeolite catalyst for sugar conversion to methyl lactate and lactic acid" 2013 *ChemSusChem.*, 6:1352-1356.

Jordan, "Biodegradation of ionic liquids: a critical review" 2015 *Chem. Soc. Rev.*, 44:8200-8237.

Kocal, "Production of linear alkylbenzenes" Nov. 2001 *Appl. Catal. A*, 22/:295-301.

Kore, "Synthesis of industrially important aromatic and heterocyclic ketones using hierarchical ZSM-5 and Beta zeolites" Mar. 2015 Applied Catalysis A: General, 493:129-141.

Kraus, "A direct synthesis of renewable sulfonate-based surfactants" 2013 *Surfact. Deterg.*, 16:317-320.

Ma, "Positional isomers of linear sodium dodecyl benzene sulfonate: Solubility, self-assembly, and air/water interfacial activity" Oct. 2006 *Langmuir*, 22:8646-8654.

Maduskar, "Quantitative carbon detector (QCD) for calibration-free, high-resolution characterization of complex mixtures" 2015 *Lab Chip*, 15(2):440-447.

Maneedaeng, "Modeling of precipitation phase boundaries in mixed surfactant systems using an improved counterion binding model" 2012 *J. Surfactants Deterg.*, 15:523-531.

Manojlović, "The Krafft Temperature of Surfactant Solutions" 2012 *Thermal Science*, 16:S631-S640.

Marshall, "Total Synthesis of the Pseudopterane(±)-Kallolide B" 1995 *J Org Chem.*, 60:796-797.

Marshall, "Total Synthesis of the Pseudopterane (−)-Kallolide B, the Enantiomer of Natural ( +)-Kallolide B" 1996 *J Org Chem.*, 61:5729-5735.

Mestres, "A green look at the aldol reaction" 2004 *Green Chem.*, 6:583-603.

Mihelj, "Temperature-dependent IR spectroscopic and structural study of 18 crown-6 chelating ligand in the complexation with sodium surfactant salts and potassium picrate" 2014 *Spectrochim Acta A Mol Biomol Spectrosc.*, 24(124):12-20.

Modler, "Linear Alkylate Sulfonates" 1996 CEH Marketing Research Report, SRI International.

National Center for Biotechnology Information, National Library of Medicine, National Institutes of Health, Accession No. 1002972-47-5, Bethesda, MD [retrieved on Feb. 9, 2017]. 1 pg.

National Center for Biotechnology Information, National Library of Medicine, National Institutes of Health, Accession No. 1135302-36-1, Bethesda, MD [retrieved on Feb. 9, 2017]. 1 pg.

National Center for Biotechnology Information, National Library of Medicine, National Institutes of Health, Accession No. 1268022-52-1, Bethesda, MD [retrieved on Feb. 9, 2017]. 1 pg.

National Center for Biotechnology Information, National Library of Medicine, National Institutes of Health, Accession No. 1368050-97-8, Bethesda, MD [retrieved on Feb. 9, 2017]. 1 pg.

National Center for Biotechnology Information, National Library of Medicine, National Institutes of Health, Accession No. 1368322-89-7, Bethesda, MD [retrieved on Feb. 9, 2017]. 1 pg.

National Center for Biotechnology Information, National Library of Medicine, National Institutes of Health, Accession No. 1369346-21-3, Bethesda, MD [retrieved on Feb. 9, 2017]. 1 pg.

National Center for Biotechnology Information, National Library of Medicine, National Institutes of Health, Accession No. 1487002-28-7, Bethesda, MD [retrieved on Feb. 9, 2009]. 1 pg.

National Center for Biotechnology Information, National Library of Medicine, National Institutes of Health, Accession No. 1547109-89-6, Bethesda, MD [retrieved on Feb. 9, 2017]. 1 pg.

National Center for Biotechnology Information, National Library of Medicine, National Institutes of Health, Accession No. 1552249-05-4, Bethesda, MD [retrieved on Feb. 9, 2017]. 1 pg.

National Center for Biotechnology Information, National Library of Medicine, National Institutes of Health, Accession No. 1690924-09-4, Bethesda, MD [retrieved on Feb. 9, 2017]. 1 pg.

National Center for Biotechnology Information, National Library of Medicine, National Institutes of Health, Accession No. 1692327-84-6, Bethesda, MD [retrieved on Feb. 9, 2017]. 1 pg.

National Center for Biotechnology Information, National Library of Medicine, National Institutes of Health, Accession No. 1692517-27-3, Bethesda, MD [retrieved on Feb. 9, 2017]. 1 pg.

National Center for Biotechnology Information, National Library of Medicine, National Institutes of Health, Accession No. 1693868-96-0, Bethesda, MD [retrieved on Feb. 9, 2017]. 1 pg.

National Center for Biotechnology Information, National Library of Medicine, National Institutes of Health, Accession No. 1694149-44-4, Bethesda, MD [retrieved on Feb. 9, 2017]. 1 pg.

National Center for Biotechnology Information, National Library of Medicine, National Institutes of Health, Accession No. 1695029-38-9, Bethesda, MD [retrieved on Feb. 9, 2017]. 1 pg.

National Center for Biotechnology Information, National Library of Medicine, National Institutes of Health, Accession No. 1697631-65-4, Bethesda, MD [retrieved on Feb. 9, 2017]. 1 pg.

National Center for Biotechnology Information, National Library of Medicine, National Institutes of Health, Accession No. 1699160-40-1, Bethesda, MD [retrieved on Feb. 9, 2017]. 1 pg.

National Center for Biotechnology Information, National Library of Medicine, National Institutes of Health, Accession No. 1702812-08-5, Bethesda, MD [retrieved on Feb. 9, 2017]. 1 pg.

National Center for Biotechnology Information, National Library of Medicine, National Institutes of Health, Accession No. 1780282-51-0, Bethesda, MD [retrieved on Feb. 9, 2017]. 1 pg.

National Center for Biotechnology Information, National Library of Medicine, National Institutes of Health, Accession No. 1781752-49-5, Bethesda, MD [retrieved on Feb. 9, 2017]. 1 pg.

(56) References Cited

OTHER PUBLICATIONS

National Center for Biotechnology Information, National Library of Medicine, National Institutes of Health, Accession No. 1781764-76-8, Bethesda, MD [retrieved on Feb. 9, 2017]. 1 pg.
National Center for Biotechnology Information, National Library of Medicine, National Institutes of Health, Accession No. 1781768-SS.8, Bethesda, MD [retrieved on Feb. 9, 2017]. 1 pg.
National Center for Biotechnology Information, National Library of Medicine, National Institutes of Health, Accession No. 1782.n9-50--3, Bethesda, MD [retrieved on Feb. 9, 2017]. 1 pg.
National Center for Biotechnology Information, National Library of Medicine, National Institutes of Health, Accession No. 1782604-69-6, Bethesda, MD [retrieved on Feb. 9, 2017]. 1 pg.
National Center for Biotechnology Information, National Library of Medicine, National Institutes of Health, Accession No. 1784189-65-6, Bethesda, MD [retrieved on feb. 9, 2017]. 1 pg.
National Center for Biotechnology Information, National Library of Medicine, National Institutes of Health, Accession No. 654683-7_1, Bethesda, MD [retrieved on Feb. 9, 2017]. 1 pg.
National Center for Biotechnology Information, National Library of Medicine, National Institutes of Health, Accession No. 853018-15-2, Bethesda, MD [retrieved on Feb. 9, 2017]. 1 pg.
National Center for Biotechnology Information, National Library of Medicine, National Institutes of Health, Accession No. 1697380-32-7, Bethesda, MD [retrieved on Feb. 9, 2017]. 1 pg.
NEWSAM, "The zeolite cage structure" Mar. 1986 *Science*, 231:1093-1099.
Nowak, "The remobilization of metals from iron oxides and sediments by metal-EDTA complexes" 2001 *Water, Air, Soil Pollut.*, 125:243-257.
Opietnik, "Mild Friedel-Crafts Acylation of Furan with Carboxylic Acids and the Heterogeneous Catalyst Couple AlPW12O40 / Mg(OH)2" 2016 Current Organic Chemistry, 16:2739-2744.
Park, "Tunable Oleo-Furan Surfactants by Acylation of Renewable Furans" Nov. 2016 ACS Cent Sci., 2(11):820-824.
Park, "An effective one-pot conversion of acid chlorides to aldehydes and ketones" Jun. 2013 *Tetrahedron Letters*, 54(24):3199-3203.
Ravindar, "A Highly Efficient Access to Spiroketals, Mono-unsaturated Spiroketals, and Furans: Hg(II)-Catalyzed Cyclization of Alkyne Diols and Triols" 2011 *Organic Chemistry Letters*, 13(12):3178-3181.
Roberts, "Optimisation of the linear alkyl benzene sulfonation process for surfactant manufacture" 2003 *Org. Process Res. Dev.*, 7:172-184.
Rodriguez, "Kinetics of precipitation of surfactants. I. Anionic surfactants with calcium and with cationic surfactants" 2001 *J. Surfactants Deterg.*, 4:1-14.
Rodriguez, "Precipitation in solutions containing mixtures of synthetic anionic surfactant and soap. I. Effect of sodium octanoate on hardness tolerance of sodium dodecyl sulfate" 1998 *J. Surfactants Deterg.*, 1:321-328.
Rodriquez, "An Efficient Asymmetric Synthesis of Prostaglandin EI" Jan. 1999 *European Journal of Organic Chemistry*, Wiley-V C H Verlag Gmbh & Co. KGAA, DE, 2655-2662.
Rosen, *Surfactants and interfacial phenomena*, 3rd ed.; Wiley-Interscience: New Jersey, 2004. Cover page, title page and table of contents.
Rust, "Surfactants—A Market Opportunity Study Update," United Soybean Board, Omni Tech International, LTD, 2008.
Scamehorn, "Precipitation of mixtures of anionic surfactants. In *Mixed surfactant systems*" 1992 ACS Symposium Series, American Chemical Society: Washington DC, 1992; 501:392-401.
Scheibel, "The evolution of anionic surfactant technology to meet the requirements of the laundry detergent industry" 2015 *J. Surfactants Deterg.*, 7(4):319-328.
Schramm, "Surfactants and their applications" 2003 Marangoni, *Annu. Rep. Prog. Chem., Sect. C*, 99:3-48.
Schulte, "Thiophene and Selenophene aus a-Propinyl-carbonyl-Verbindungen" 1968 *Chem Ber.*, 101:1540-1552.
Scott, "The biodegradation of surfactants in the environment" 2000 *Biochim. Biophys. Acta, Biomembr.*, 1508:235-251.
Scully, "The Sulfonation of Furan and Furan Homologs. Preparation of Furansulfonamides" 1954 *Org. Chem.*, 19(6):894-901.
Setzkorn, "An evaluation of the river die-away technique for studying detergent biodegradability" 1964 *Am. Oil Chem. Soc.*, 41:826-830.
Shea, "Reversal of cation-induced reduction in glyphosate activity with EDTA" 1984 *Weed Sci.*, 32:802-806.
Shirke, "Modular Assembly of Furotropones and Benzofurotropones, and Study of Their Physicochemical Properties" 2015 *J Org Chem.*, 80:4893-4903.
Showell, *Handbook of detergents, part D: Formulation*; vol. 128, CRC Press Taylor & Francis Group: Florida, 2006. Cover page, title page and table of contents.
Smith, "y-Selective directed catalytic asymmetric hydroboration of 1,1- disubstituted alkenes" 2012 *Chem Commun.*, 48:12180-12182.
Smyth, "Toward a clean alternative to Friedel—Crafts acylation: In situ formation, observation, and reaction of an acyl bis(trifluoroacetyl)phosphate and related structures" 1998 *J. Org. Chem.*, 63:8946-8951.
Snatzke: "Circular dichroism-XLVI" Jan. 1971 Tetrahedron, Elsevier Science Publishers, Amsterdam, NL, 15(27):3645-3653.
Sorrenti, "Amphiphiles in aqueous solution: well beyond a soap bubble." Nov. 2013 *Chem. Soc. Rev.*, 42:8200-8219.
Tago, "Selective production of isobutylene from acetone over alkali metal ion-exchanged BEA zeolites" 2011 *Catal. Today*, 164:158-162.
Tedder, "The use of trifluoroacetic anhydride and related compounds in organic syntheses" 1955 *Chem. Rev.*, 55:787-827.
Tius, "A Synthesis of 2-Alkyl-3-Furioc Acids" 1985 *Tetrahed. Letters*, 26(31): 3635-3638.
Tsai, "Development of a green LAB process: alkylation of benzene with 1-dodecene over mordenite" 2003 *Green Chem.*, 5:404-409.
Vautier-Giongo, "Estimate of the Ionization Degree of Ionic Micelles Based on Krafft Temperature Measurements" 2003 *Phys. Chem. B*, 107: 5398-5403.
Vlachy, "Role of surfactant headgroup on the counterion specificity in the micelle-to-vesicle transition through salt addition" 2008 *J. Colloid Interface Sci.*, 319:542-548.
Watry, "Comparison of the adsorption of linear alkanesulfonate and linear alkylbenzenesulfonate surfactants at liquid interfaces" 2000 *J. Am. Chem. Soc.*, 122:875-883.
Zimmerman, "Design of hard water stable emulsifier systems for petroleum and bio-based semi-synthetic metalworking fluids" 2003 *Environ. Sci. Technol.*, 37:5278-5288.
Bartoli, "SiO 2-Supported CeCI 3 . 7H 2 O-Nal Lewis Acid Promoter: Investigation into the Garcia Gonzalez Reaction in Solvent-Free Conditions [bottom]" Aug. 2007 Journal of Organic Chemistry, 72(16):6029-6036.
D'Auria, "Synthesis of 4-ylidenebutenolides and 4-oxo-2-enoic acid methyl esters from 5-methoxy-2-furyl carbinols" Jan. 1980 Tetrahedron, 36(20-21):3071-3074.
El Dessouky, "Radiolysis of 1-(2-furanyl)-1-pentanone in the presence of atmospheric oxygen" Oct. 1985 Journal of Radioanalytical and Nuclear Chemistry, 92(1):51-57.
Gensler, "1,4-Diketones from skipped acetylenes" Oct. 1978 Journal of Organic Chemistry, 43(21):4081-4085.
Kawabe, "Studies on Alkylated Furan Derivatives. III. Synthesis and Antimicrobial Activity of 5-Alkyl-2-furamide and 5-Alkyl-N-alkyl-2-furamide", 1960 Yakugaku Zasshi, 80(1960):58-62.
Nazorova, "610 Khimiya Geterotsiklicheskikh Soedinenii Letters to the Editor Organolithium Compounds of Pyromucic Acid and of Furyural Acetals" Jan. 1967 Dictionary of Organic Compounds [Russian Translation], 3(4):610.
Ohta, "The birch reduction of heterocyclic compounds V Birch reduction of 2- and 5-acylfuran-3-carboxylic acids and reductive elimination of 2-arylmethoxymethyl)furan-3-carboxylic acids" Jul. 2000 Journal of Heterocyclic Chemistry, 37(4);751-755.
Piao, "Synthesis of 9-(5-pentyl-2-furyl)nonanoic acid" Jan. 1999 Chinese Chemical Letters, Elsevier, Amsterdam, NL, 10(9):737-738.

(56) References Cited

OTHER PUBLICATIONS

Ragan, "Investigation of Methods for Seven-Membered Ring Synthesis: A Practical Synthesis of 4-Oxo-5,6,7,8-tetrahydro-4H-cyclohepta[b]furan-3-carboxylic Acid" Jul. 2001 *Org. Proc. Res. Dev.*, 5(5):498-507.

Robinson, "Directive Effects in Acylation of Methyl Furan-2-carboxylate" Dec. 1966 Journal of Organic Chemistry, 31(12):4252-4252.

Park et al., "Tunable Oleo-Furan Surfactants by Acylation of Renewable Furans," *ACS Cent. Sci.*, 2016; 2:820-824.

National Center for Biotechnology Information, National Library of Medicine, National Institutes of Health, Accession No. 1781768-58-8, Bethesda, MD [retrieved on Feb. 9, 2017]. 1 pg.

National Center for Biotechnology Information, National Library of Medicine, National Institutes of Health, Accession No. 1782779-50-3, Bethesda, MD [retrieved on Feb. 9, 2017]. 1 pg.

National Center for Biotechnology Information, National Library of Medicine, National Institutes of Health, Accession No. 654683-71-3, Bethesda, MD [retrieved on Feb. 9, 2017]. 1 pg.

\* cited by examiner

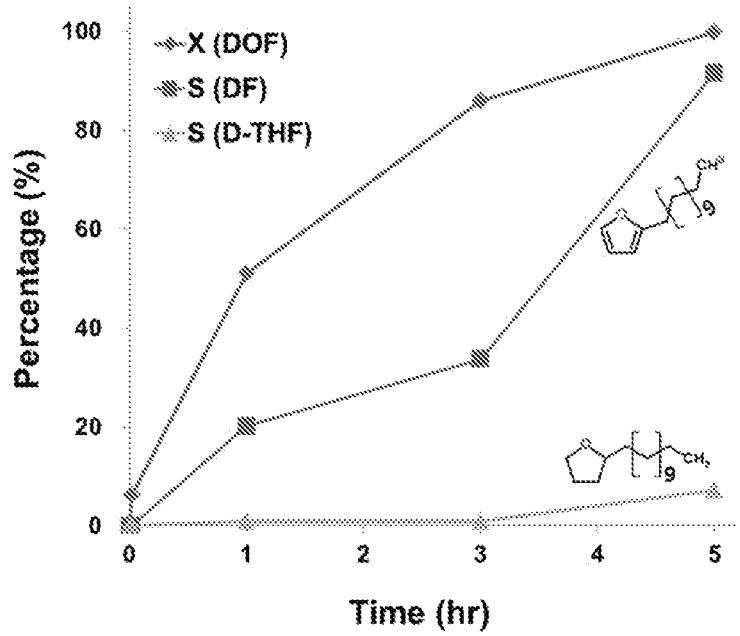

METHODS OF FORMING AROMATIC CONTAINING COMPOUNDS

PRIORITY

This application is the § 371 U.S. National Stage of International Application No. PCT/US2016/060774, filed 7 Nov. 2016, entitled Methods of Forming Aromatic Containing Compounds, which claims priority to U.S. Provisional Application No. 62/252,200 filed on Nov. 6, 2015 entitled Methods of Forming Aromatic and Linear Chain Containing Compounds, the entire disclosure of which is incorporated herein by reference thereto.

GOVERNMENT SUPPORT

This invention was made with government support under DE-SC0001004 awarded by the Department of Energy. The government has certain rights in the invention.

SUMMARY

Disclosed herein are methods that include acylating an aromatic containing compound by reacting the aromatic containing compound with an anhydride containing compound to form an acylated aromatic containing compound.

Also disclosed are methods that include acylating an aromatic containing compound by reacting the aromatic containing compound with an anhydride containing compound to form an acylated compound; hydrogenating the acylated compound to replace ketone functionality with an alkyl functionality; and functionalizing the acylated compound with a hydrophilic group containing compound to form a surfactant.

Also disclosed are methods that include acylating a furan containing compound by reacting the furan containing compound with an anhydride containing compound to form an acylated compound; hydrogenating the acylated compound to replace ketone functionality with an alkyl functionality; converting the acylated furan containing compound to an acylated benzene containing compound; and functionalizing the acylated compound with a hydrophilic group containing compound to form a surfactant.

Also disclosed are methods that include acylating an aromatic containing compound by reacting the aromatic containing compound with an anhydride containing compound to form an acylated aromatic containing compound; and functionalizing the acylated aromatic containing compound with a hydrophilic moiety Also disclosed are methods that include acylating an aromatic containing compound by reacting the aromatic containing compound with an anhydride containing compound to form an acylated aromatic containing compound; hydrogenating the acylated compound to replace a ketone group with a methylene group; and functionalizing the acylated aromatic containing compound with a hydrophilic moiety Also disclosed are methods that include acylating an aromatic containing compound by reacting the aromatic containing compound with an anhydride containing compound to form an acylated aromatic containing compound; subjecting the acylated aromatic containing compound to a cycloaddition reaction; and functionalizing the acylated aromatic containing compound with a hydrophilic moiety.

Also disclosed are methods that include acylating an aromatic containing compound by reacting the aromatic containing compound with an anhydride containing compound to form an acylated aromatic containing compound; subjecting the acylated aromatic containing compound to a cycloaddition reaction; adding an alkyl group to the group added via acylation of the aromatic containing compound; hydrogenating the acylated compound to replace a ketone group with a methylene group; and functionalizing the acylated aromatic containing compound with a hydrophilic moiety.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIGS. 5A and 5B show time-on-stream results (conversion of 2-dodecanoylfuran and selectivities of 2-dodecylfuran and 2-dodecyl tetrahydrofuran) for the hydrogenation of 2-dodecanoylfuran in 100 (FIG. 5A) and 350 psi (FIG. 5A) of $H_2$.

DETAILED DESCRIPTION

Figure 1A:
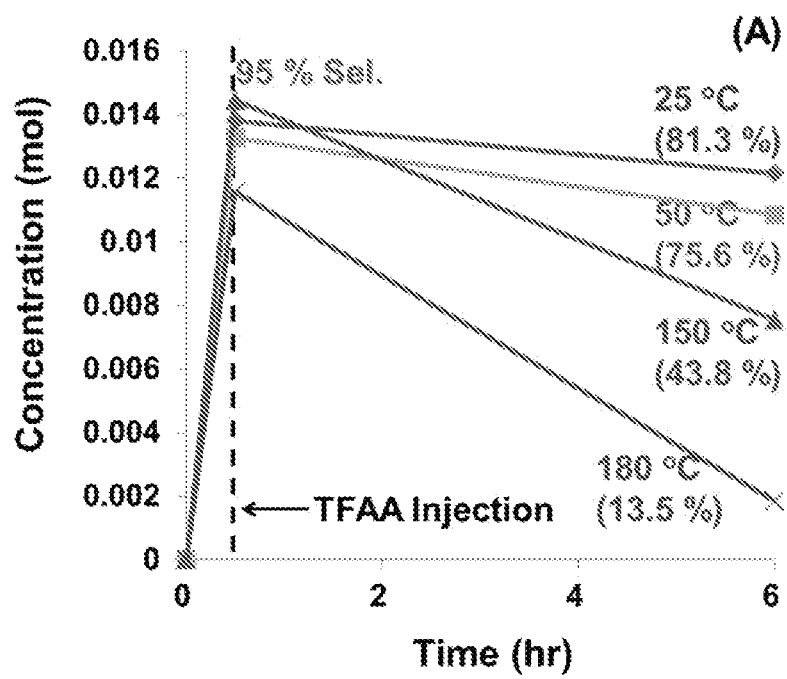
FIGS. 1A and 1B shows the change of concentrations of 2-dodecanoylfuran (FIG. 1A) and lauric acid (FIG. 1B) during reaction (Reaction Conditions: 200 psi ($N_2$), 0.014 mols of Furan, 0.018 mols of lauric acid, and 0.028 mols of TFAA in hexane (10 mL), HBEA 0.2 g, 6 hrs).

One skilled in the art will appreciate that the methods described herein can be practiced with embodiments other than those disclosed. The disclosed embodiments are presented for purposes of illustration and not limitation. One will also understand that components of the methods depicted and described with regard to the figures and embodiments herein may be interchangeable.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like. For example, a conductive trace that "comprises" silver may be a conductive trace that "consists of" silver or that "consists essentially of" silver.

As used herein, "consisting essentially of," as it relates to a composition, apparatus, system, method or the like, means that the components of the composition, apparatus, system, method or the like are limited to the enumerated components and any other components that do not materially affect the basic and novel characteristic(s) of the composition, apparatus, system, method or the like.

The words "preferred" and "preferably" refer to embodiments that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Also herein, the recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" a particular value, that value is included within the range.

Use of "first," "second," etc. in the description above and the claims that follow is not intended to necessarily indicate that the enumerated number of objects are present. For example, a "second" substrate is merely intended to differentiate from another infusion device (such as a "first" substrate). Use of "first," "second," etc. in the description above and the claims that follow is also not necessarily intended to indicate that one comes earlier in time than the other.

As used herein, "alkyl" is an unsubstituted or substituted saturated hydrocarbon chain radical having from 1 to about 12 carbon atoms; from 1 to about 10 carbon atoms; from about 1 to about 6 carbon atoms; or from about 1 to about 4 carbons. It should also be understood that an alkyl moiety can be a combination of two or more alkyl moieties. Illustrative, non-limiting examples of alkyl groups include, for example, methyl, ethyl, propyl, iso-propyl, and butyl. A $C_2$ to $C_4$ substituted or unsubstituted alkyl radical, for example refers to a $C_2$ to $C_4$ linear alkyl chain that may be unsubstituted or substituted. If the $C_2$ to $C_4$ linear alkyl chain is substituted with an alkyl radical, the carbon number of the alkyl radical increases as a function of the number of carbons in the alkyl substituent.

As used herein, "anhydride" refers to a chemical compound that includes two acyl (a function group derived by the removal of one or more hydroxyl groups from an oxoacid, it contains a double bonded oxygen atom and an alkyl group (e.g., RC(=O), where R is an alkyl group) groups bonded to the same oxygen atom (—(O=)COC(=O)—). The anhydride can have any types of alkyls bonded to the two terminal carbons, and the two alkyls need not be the same.

As used herein, "aromatic" refers to a major group of unsaturated cyclic hydrocarbons containing one or more rings. An aromatic group may contain carbon (C), nitrogen (N), oxygen (O), sulfur (S), boron (B), or any combination thereof. At least some carbon is included. Aromatic includes both aryl and heteroaryl rings. The aryl or heteroaryl ring may be further substituted by additional aliphatic, aromatic, or other radicals. Illustrative five membered aromatic groups can include, for example furan, thiophene, pyrrole, imidazole, triazole, dithiole, oxathiole, isoxazole, oxazole, thiazole, isothiazole, and oxadizole. Illustrative six membered aromatic groups can include, for example benzene, pyridine, pyran, dioxin, pyridazine, pyrimidine, pyrazine, triazine, and oxazine. Illustrative double ring aromatics include, for example, naphthalene, tetrahydronapthalene, indene, isoindene, benzofuran, isobenzofuran, benzothiophene, indole, quinolone, isoquinoline, quinazoline, anthracene, and phenanthrene for example. In some embodiments, aromatic groups may include furan, thiophene, pyrrole, imidazole, benzene, pyridine, naphthalene, and tetrahydronaphthalene. In some embodiments, aromatic groups may include furan, thiophene, and pyrrole. In some embodiments, aromatic groups may include furan. In some embodiments, aromatic groups may include benzene. An aromatic containing compound refers to a compound that includes an aromatic group, as discussed above. The aromatic containing compound may also additional include any other groups or atoms.

As used herein, "hydrophilic" refers to a water soluble portion of a molecule that can either carry a formal charge, ionic, or can be neutral, non-ionic. As used herein, "ionic" means a hydrophilic group that carries a formal positive charge, negative charge or both. As used herein, "anionic" means a hydrophilic group that is typically a neutralized acid and has a negative charge that is balanced by a positive counterion. Anionic hydrophilic groups are the most commonly used type of hydrophilic group in surfactants. Typical anionic hydrophilic groups include but are not limited to the sodium (Na+) form of carboxylic acids, sulfates, sulfonates, and phosphates. As used herein, "cationic" means a hydrophilic group that has a positive charge and is balanced by a negative counter ion, for example chloride (Cl−). Typical cationic hydrophilic groups are quaternary ammonium compounds that contain a nitrogen group bound to 4 other atoms. As used herein, "zwitterionic" means a hydrophilic groups that contains both cationic and anionic groups. As used herein, "nonionic" means a hydrophilic group that does not contain a formal charge like the ionic groups. Typically, nonionic groups contain carbon, hydrogen, oxygen and nitrogen, with the most common form being based on ethylene oxide to form ethoxylates. The ethoxylate hydrophilic group is typically connected via an ether linkage to the rest of the molecule, but can also be connected via an ester, amine, or amide linkage. Other nonionic groups can be amine ethoxylates, polyols and polyol derivatives, such as glycerol, propanediol, xylitol, sorbitol, mono and polysaccharide derivatives, such as glucose, sucrose, maltose, or xylose derivatives, and polyol amines, such as glucamine or xylosamine.

As used herein, "hydrophobic" means a portion of a molecule that is generally insoluble in water and is usually a hydrocarbon. A hydrocarbon generally refers to an alkyl chain. In some embodiments, a hydrocarbon can refer to a moiety that can include between 3 and 26 carbons, in some embodiments from 6 to 26 carbons. The hydrocarbon can be linear, branched, cyclic or any combination thereof. In some embodiments, a hydrocarbon can include only carbon and hydrogen atoms and in some embodiments it could be substituted with one or more groups. The hydrocarbon can be saturated (there are only single bonds in the hydrocarbon) or unsaturated (there is at least one double or triple bond in the hydrocarbon).

As used herein, "hydroxyl group" refers to a substituent group of formula —OH.

As used herein, "ketone" refers to the group C=O that is bonded to two other atoms, and methylene refers to the group $CH_2$ that is also bonded to two other atoms (e.g., it is saturated).

Unless otherwise stated, as employed herein, when a moiety (e.g., alkyl, or alkenyl) is described as "substituted" it is meant that the group optionally has from one to four, from one to three, or one or two, non-hydrogen substituents. Suitable substituents include, without limitation, halo, hydroxy, oxo (e.g., an annular —CH— substituted with oxo is —C(O)—), nitro, halohydrocarbyl, hydrocarbyl, aryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups.

For any method disclosed herein that includes discrete steps, the steps may be conducted in any feasible order, unless context indicates otherwise. And, as appropriate, any combination of two or more steps may be conducted simultaneously.

All headings are for the convenience of the reader and should not be used to limit the meaning of the text that follows the heading, unless so specified.

The complete disclosure of all patents, patent applications, and publications, and electronically available material cited herein are incorporated by reference in their entirety.

New methods of synthesizing compounds are always needed as different precursors can then be used, different reagents can then be used, and/or different byproducts are produced, for example. Disclosed herein are new methods of forming aromatic and alkyl chain containing compounds that include an acylation step. In some embodiments, a method can include acylating an aromatic containing compound by reacting the aromatic containing compound with an anhydride containing compound to form an acylated aromatic containing compound.

In some embodiments, methods can include one or more of the following steps, carried out in any order: include acylating an aromatic containing compound by reacting the aromatic containing compound with an anhydride containing compound to form an acylated aromatic containing compound; subjecting an acylated compound to hydrogenation to replace the ketone functionality with an alkyl; functionalizing an acylated aromatic containing compound with a hydrophilic group containing compound; and converting an acylated five membered aromatic ring containing compound to an acylated six membered aromatic ring containing compound (or any increase of the aromatic ring size). In some methods, another step can be carried out at any point in the method: adding an additional side chain to the hydrophobic group, for example via an aldol-condensation. All of these method steps will be discussed below.

Illustrative aromatic containing compound can include aromatic moieties such as those illustrated below in Table 1 below.

TABLE 1

Aromatic moieties

| Furan |
| Thiophene |
| Pyrrole |
| Imidazole |
| Benzene |
| Pyridine |
| Naphthalene |
| Tetrahydronaphthalene | wherein, $R^n$ (n=1-8) either denotes a point of attachment for a hydrophobic group, the hydrophilic group, a hydrocarbon chain with a carbon number between 1 and 10 between the aromatic group and the hydrophilic group, or a hydrogen atom for example.

One step in disclosed methods includes acylating an aromatic containing compound by reacting the aromatic containing compound with an anhydride containing compound to form an acylated aromatic containing compound. The aromatic containing compound that is being acylated may or may not have previously been subjected to any other steps disclosed herein. Acylating an aromatic containing compound adds an acyl group to the aromatic containing compound to produce an acylated aromatic compound. The compound providing the acyl group can be referred to as the acylating agent. An anhydride, as it includes two acyl groups, can be an effective acylating agent.

The acylating agent, e.g., the anhydride can be added to the aromatic containing compound or in some embodiments, compounds that can be reacted to form an anhydride can be added to an aromatic containing compound (or a mixture containing an aromatic containing compound). For example, a fatty acid could be reacted with a compound in order to form the eventual acylating agent. More specifically, for example, a fatty acid could be reacted with an acyl containing compound, or even more specifically an anhydride to form a long chain (e.g., hydrophobic) containing anhydride. An example of such a reaction can be seen in part B of Scheme 1. In some specific embodiments, a fatty acid could be reacted with an anhydride, for example trifluoroacetic anhydride (TFAA), or acetic anhydride. TFAA may be advantageous because the fluorines contained therein are very electronegative and therefore easily form the desired lauric anhydride (for example). Furthermore, TFAA can be recycled, as shown in part C of Scheme 1.

In some embodiments, if for example acetic anhydride is utilized (to react with a fatty acid), a mix of anhydride products would be formed, where some products include two long-chain alkyl groups, some products contain one long chain alkyl group and one acetyl group, and some remain as acetic anhydride.

In some advantageous embodiments, the formation of the acylating agent and the reaction of the aromatic containing compound with the acylating agent can occur at substantially the same time, e.g., in the same "pot". This is represented by part A+B in Scheme 1. More specifically, in some embodiments, a single reaction vessel could be utilized to combine the aromatic containing compound, a fatty acid, and an anhydride to "simultaneously" form the acylating agent and acylate the aromatic containing compound.

In some embodiments, an acylating agent can be chosen such that the acylation of the aromatic containing compound with the acylating agent adds an acyl group that contains an alkyl group to the aromatic containing compound. In some embodiments, the alkyl group added via acylation could be a hydrophobic group or could be converted into a hydrophobic group.

Acylating an aromatic containing compound can be undertaken, in some embodiments, by simply combining the acylating agent and the aromatic containing compound. In some embodiments, one or more reaction conditions or reagents can be modified or added respectively. In some embodiments, a catalyst can be utilized and in some embodiments no catalyst is utilized. In some embodiments, the pressure that the reaction is occurring under can be modified, for example it could be increased from atmospheric pressure. The pressure that the acylation reaction can be carried out at can be from 0 to 3000 psi, for example. In some embodiments, the temperature that the acylation reaction is occurring at can be modified, for example, it could be increased from room temperature. The temperature that the acylation reaction can be carried out at can be from 0° to 700° C., for example. The reaction can be carried out heterogeneously or homogeneously in the gas, liquid, or solid phases or any combination of phases or supercritical conditions.

The acylation reaction can optionally be carried out with use of a catalyst. Table 2 provides illustrative potential catalyst species that can be used.

TABLE 2

Potential catalyst classes and types which can be used in all four chemical reactions presented.

| Family | Genus | Species | Example |
|---|---|---|---|
| Acid | Lewis Acid (L-Acid) Catalysts | L-Acid | $AlCl_3$, $TiCl_4$, $FeCl_3$, $BF_3$, $SnCl_4$, $ZnCl_2$, $ZnBr_2$, Amberlyst-15 |
| | | Supported L-Acid L-Acid/S | $SiO_2$, $Al_2O_3$, $ZrO_2$, $TiO_2$, $SiO_2$—$Al_2O_3$ |
| | BrØnsted Acid (B-Acid) Catalysts | B-Acid | HCl, HBr, HI, $HClO_4$, $HClO_3$, $HNO_3$, $H_2SO_4$, $CH_3COOH$, $CF_3COOH$, $H_3PO_4$ |
| | Solid Acid Catalysts | Zeolites, (Z) | H-ZSM-5, H-BEA, H-Y, Mordenite, Ferrierite |
| | | Substituted-Zeolites (Sub.) | Sn, Ge, Ti, Fe, Zr |
| | | Heteropolyacids (HPAs) | $H_3PW_{12}O_{40}$, $H_3SiW_{12}O_{40}$, $H_3PMo_{12}O_{40}$, $H_3SiMo_{12}O_{40}$ ($Cs^+$ substituted HPAs) |
| | | Phosphate ($PO4^{3-}$) | Niobium phosphate ($NbOPO_4$), Zirconium phosphate ($ZrO_2$—$PO_4$), Siliconiobium phosphate (Nb—P—Si—O) |
| | | Zirconia ($ZrO_2$) | $SO_3$—$ZrO_2$, $SiO_2$—$ZrO_2$, Zeolites-$ZrO_2$, $Al_2O_3$—$ZrO_2$, $WO_x$—$ZrO2$ |
| | | Carbon (C) | Sulfated carbon ($SO_3H$-functionalized carbon) |
| Base | Solid Base Catalysts | Supported Alkalis | $KF/Al_2O_3$, $K_2CO_3/Al_2O_3$, $KNH_2/Al_2O_3$, $NaOH/Al_2O_3$, $KOH/Al_2O_3$ |
| | | Zeolites, Clays | K, Rb, Cs-exchanged X-zeolites, ETS-10, Sepiolite, |

TABLE 2-continued

Potential catalyst classes and types which can be used in all four chemical reactions presented.

| Family | Genus | Species | Example |
|---|---|---|---|
| | | Phosphates | Hydroxyapatite, natural phosphates |
| | | Amides, imines, amines, or ammonium ions on support | KNH2/Al2O3, K, Y, Eu supported on zeolites |
| | | Metal Oxide, Mixed Metal Oxide | MgO, CaO, Mg—Zr—O, Mg—Si—O, Mg—Al—O |
| | Homogeneous Base | Organic & Inorganic | pyridine, imidazole, ammonia |
| Metal | Metallic | Precious metals, alkali or alkaline earth metals | Pt, Pd, Ni, Cu, Al, Zn, Au, Ag, Sn |
| | Bimetallic | Transition-Transition or Precious-Transition metals | Pd—Cu, Cu—Ni, Cu—Cr, Ni—Pt, Ni—Pd, Ni—Sn |
| | Metal Oxide | Metal oxides, Rare earth oxides, Alkali metal oxides | NiO, ZnO$_2$, CuO, Cu—Cr—O, Cu—Ni—O, Cu—Al—O, Al$_2$O$_3$, ZrO$_2$, La$_2$O$_3$ |

Disclosed methods can also include an optional step of subjecting an acylated compound to hydrogenation. Acylation of the aromatic containing compound will necessarily introduce a ketone adjacent the aromatic ring. Hydrogenation serves to replace the ketone functionality with a methylene.

Any method of hydrogenation, e.g., replacing a ketone with an alkyl can be utilized in disclosed methods. In some embodiments, the acylated aromatic containing compound can be reacted with hydrogen (H$_2$) gas. In some embodiments, one or more reaction conditions or reagents can be modified or added respectively. In some embodiments, a catalyst can be utilized and in some embodiments no catalyst is utilized. Any of the illustrated catalysts presented above in Table 2, or others can optionally be utilized in the hydrogenation reaction. In some embodiments, the pressure that the reaction is occurring under can be modified, for example it could be increased from atmospheric pressure. The pressure that the hydrogenation reaction can be carried out at can be from 0 to 3000 psi, for example. In some embodiments, the temperature that the hydrogenation reaction is occurring at can be modified, for example, it could be increased from room temperature. The temperature that the hydrogenation reaction can be carried out at can be from 0° to 700° C., for example. The reaction can be carried out heterogeneously or homogeneously in the gas, liquid, or solid phases or any combination of phases or supercritical conditions.

Disclosed methods can also include an optional step of functionalizing an acylated aromatic containing compound with a hydrophilic moiety containing compound. It should also be noted that disclosed methods could include functionalizing an aromatic containing compound before it is acylated.

In some embodiments, the hydrophilic moiety can be chosen to produce a desired final compound. For example, the choice of hydrophilic moiety can determine if an ionic, anionic, cationic or otherwise surfactant is being synthesized. If an ionic (anionic and cationic) surfactant is being synthesized, the hydrophilic moiety can include a surface active ion and a counter metal ion which can include but are not limited to those seen in Table 3 below.

TABLE 3

Ionic Moieties

| Anionic | | Cationic | |
|---|---|---|---|
| Sulfate | R—O—S(=O)$_2$—O$^-$ | Amines & Ammonium salts | R—S$^+$(R')(R'')—, cyclic ammonium structures |
| Sulfonate | R—S(=O)$_2$—O$^-$ | Polyammonium | [R—N$^+$(R')—R''—N$^+$(R')—R'']$_n$ |
| Sulfinate | R—S(=O)—O$^-$ | Hydroxammonium | R—N$^+$(OH)(R')—R' |
| Thiosulfate | R—O—S(=O)(=S)—O$^-$ | Pyridinium | pyridinium-N$^+$—R |

TABLE 3-continued

Ionic Moieties

| Anionic | | Cationic | |
|---|---|---|---|
| Sulfamidate | R—NH—S(=O)(=O)—O⁻ | Picolinium | R'-substituted pyridinium N⁺—R |
| Carboxylate | R—C(=O)—O⁻ | Imidazolinium | Imidazolium ring with N⁺ substituted by R, R', R' |
| Sarcosinate & Taurate | R—N(R')—R'—C(=O)(O⁻)(O⁻) | Benzimidazolinium | Benzimidazolium with R', R, R' substituents |
| Phosphate | R—O—P(=O)(O⁻)—O⁻ or R—O—P(=O)(O⁻)—O—R' | Oxonium | R—O⁺(R')—R'' |
| Pyrophosphate | R—O—P(=O)(O⁻)—O—P(=O)(O⁻)—O—R' | Sulfonium | R—S⁺(R')—R'' |
| Phosphonate | R—P(R')(=O)—O⁻ or R—P(=O)(O⁻)—O⁻ | Phosphonium | R—P⁺(R')(R'')—R''' |

| Counter-ion | |
|---|---|
| Na⁺, K⁺, Li⁺, Ca²⁺, Mg²⁺, NH₄⁺, amines | Cl⁻, Br⁻, NO₃⁻, SO₄²⁻, PO₄³⁻, HPO₄²⁻, H₂PO₄⁻, CH₃OSO₃⁻, HCO₂⁻, CH₃CO₂ | wherein, R denotes either the point of attachment of the ion to the aromatic group or to a hydrocarbon chain, with or without oxygen atoms, ($-(CH_2)_n-$ or $-(CH_2CH_2O)_n-$) attached to the aromatic group wherein n is 1 to 10. R', R" and R''' represent either a hydrogen atom or a hydrocarbon chain with a carbon number between 1 and 10 and X denotes a heteroatom.

If a nonionic surfactant is being synthesized, the hydrophilic moiety can include those seen in Table 4 below.

TABLE 4

| Non-ionic moieties | |
|---|---|
| Polyethoxylate | R—(OCH₂CH₂)$_n$—OR |
| Poly(Oxyethylene-co-Oxypropylene) | |
| 1 | R—(OCH₂CH₂)$_m$—(OCH(CH₃)CH₂)$_n$—(OCH₂CH₂)$_m$—OH |
| 2 | R—(OCH₂CH₂)$_n$—(OCH(CH₃)CH₂)$_m$—(OCH(CH₃)CH₂)$_n$—OH |

TABLE 4-continued

Non-ionic moieties 1,4-Sorbitan derviatives

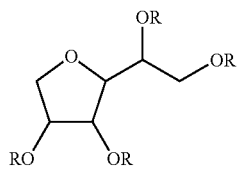

Isosorbide derivatives

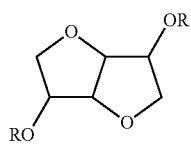

Polyglycoside

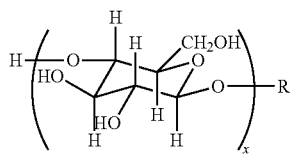

wherein, R denotes either the point of attachment to the aromatic group or a primary, secondary or tertiary amide, an ester, a hydrocarbon chain, or a hydrogen atom while n is between 1 and 40 in ethoxylates and x is between 1 and 5 in polyglycosides.

If a zwitterionic surfactant is being synthesized, the hydrophilic moiety can include zwitterionic groups. Zwitterionic groups typically include a cationic group, for example a primary, secondary, or tertiary amine or quaternary ammonium ion attached to an anionic group listed in Table 3.

In some embodiments, the hydrophilic moiety added can include, for example an anionic moiety, for example a sulfonate or a phosphate; a cationic moiety, for example a quaternary ammonium compound; a nonionic moiety, for example an alcohol or an ethoxylate; or an amphoteric moiety, for example an imidazoline or beatine.

Any method of functionalizing the acylated aromatic compound with a hydrophilic moiety containing compound or portion of a compound can be utilized herein. In some embodiments, sulfonation or phosphonation, can be utilized, for example. In some embodiments, one or more reaction conditions or reagents can be modified or added respectively. In some embodiments, a catalyst can be utilized and in some embodiments no catalyst is utilized. Any of the illustrated catalysts presented above in Table 2 above, or others can optionally be utilized in to functionalize the acylated compound with the hydrophilic moiety. In some embodiments, the pressure that the reaction is occurring under can be modified, for example it could be increased from atmospheric pressure. The pressure that the functionalization reaction can be carried out at can be from 0 to 3000 psi, for example. In some embodiments, the temperature that the reaction is occurring at can be modified, for example, it could be increased from room temperature. The temperature that the functionalization reaction can be carried out at can be from 0° to 700° C., for example. The reaction can be carried out heterogeneously or homogeneously in the gas, liquid, or solid phases or any combination of phases or supercritical conditions.

Disclosed methods can also include an optional step of cycloaddition. An illustrative cycloaddition reaction is the Diels-Alder reaction. For example, this step can convert an acylated five membered aromatic ring containing compound to an acylated six membered aromatic ring containing compound (or any increase of the aromatic ring size). Any method of cycloaddition, e.g., increasing the ring size of an aromatic group, can be utilized in disclosed methods. In some embodiments, the acylated aromatic containing compound can be reacted with ethylene ($C_2H_4$), propylene ($C_3H_6$), acrolein ($C_3H_4O$), or acrylic acid ($C_3H_4O_2$). In some embodiments, one or more reaction conditions or reagents can be modified or added respectively. In some embodiments, a catalyst can be utilized and in some embodiments no catalyst is utilized. Any of the illustrated catalysts presented above in Table 2, or others can optionally be utilized in the cycloaddition reaction. In some embodiments, the pressure that the reaction is occurring under can be modified, for example it could be increased from atmospheric pressure. The pressure that the cycloaddition reaction can be carried out at can be from 0 to 3000 psi, for example. In some embodiments, the temperature that the reaction is occurring at can be modified, for example, it could be increased from room temperature. The temperature that the cycloaddition reaction can be carried out at can be from 0° to 700° C., for example. The reaction can be carried out heterogeneously or homogeneously in the gas, liquid, or solid phases or any combination of phases or supercritical conditions.

In embodiments where the step of acylating the aromatic group containing compound has been carried out in order to, for example attach a hydrophobic group to the aromatic containing compound, another optional step can be undertaken. This optional step includes adding an alkyl chain (e.g., an alkyl chain having from 1 to 10 carbon atoms, in some embodiments from 1 to 6 carbon atoms) to the existing hydrophobic group. Any reaction that can add an alkyl chain to the existing hydrophobic group can be utilized. One such method that can be utilized can include, for example an aldol condensation reaction. An aldol condensation reaction can be utilized to add an alkyl chain to the existing hydrophobic chain if the optional hydrogenation reaction has not yet been carried out because the aldol-condensation reaction utilizes the ketone to add the alkyl chain to that carbon atom.

In some embodiments, one or more reaction conditions or reagents can be modified or added respectively. In some embodiments, a catalyst can be utilized and in some embodiments no catalyst is utilized. Any of the illustrated catalysts presented above in Table 2, or others can optionally be utilized to add an alkyl chain to the hydrophobic moiety. In some embodiments, the pressure that the reaction is occurring under can be modified, for example it could be increased from atmospheric pressure. The pressure that the reaction can be carried out at can be from 0 to 3000 psi, for example. In some embodiments, the temperature that the reaction is occurring at can be modified, for example, it could be increased from room temperature. The temperature that the reaction can be carried out at can be from 0° to 700° C., for example. The reaction can be carried out heterogeneously or homogeneously in the gas, liquid, or solid phases or any combination of phases or supercritical conditions.

Disclosed methods can be utilized to make compounds that can be used in a number of different applications, including as an illustrative and non-limiting example, surfactants. In some embodiments, such methods can include acylating an aromatic containing compound by reacting the aromatic containing compound with an anhydride containing compound to form an acylated aromatic containing compound; and functionalizing an acylated aromatic containing compound with a hydrophilic group containing compound. In some embodiments, such methods can optionally include a step of subjecting the acylated compound to hydrogenation to replace the ketone functionality with an methylene. In some embodiments, such methods can optionally include adding an additional side chain to the hydrophobic group, for example via an aldol-condensation before an optional step of hydrogenation to replace the ketone group with a methylene group.

In some embodiments, the step of acylating the aromatic containing compound can occur first, before any other steps. In some embodiments, the step of functionalizing the acylated compound with a hydrophilic group can occur immediately after the acylation step or after any other intermediate steps. In some embodiments, the step of subjecting the acylated compound to hydrogenation to replace the ketone functionality with a methylene functionality can occur before the compound is functionalized with a hydrophilic moiety. In some embodiments, the step of subjecting the acylated compound to hydrogenation can occur after an additional side chain has been added to the hydrophobic group, so that the additional side chain can be added with an aldol-condensation reaction.

Another disclosed method that could be utilized to make illustrative compounds could include acylating an aromatic containing compound by reacting the aromatic containing compound with an anhydride containing compound to form an acylated aromatic containing compound; converting the acylated aromatic ring containing compound to an acylated aromatic ring containing compound that includes at least one more carbon atom in the ring; and functionalizing the acylated aromatic containing compound with a hydrophilic group containing compound. The cycloaddition and the functionalization step can be carried out in any order after the acylation step. In some such embodiments, disclosed methods can also include an optional step of hydrogenation to replace the ketone on the hydrophobic moiety added via acylation with a methylene group. Optionally, an alkyl side chain can be added to the hydrophobic group, either before the optional hydrogenation (via an aldol-condensation reaction for example) or via some other reaction (either before or after the optional hydrogenation reaction).

In some specific, illustrative embodiments, disclosed methods can be utilized to make compounds for use as surfactants. Surfactants are an integral part of modern society and are widely used for household detergents, cleaners, emulsifiers, foaming agents and personal care. The total world market for surfactants is $30 billion and is expected to reach $40 billion in 2020 with a growth rate of 3% annually; household detergents comprise over 50% of this market. Linear alkylbenzene sulfonate (LAS) is the most widely used surfactant worldwide due to its low cost, high detergency, and biodegradability. Due to its high biodegradability, the applications for LAS are rapidly increasing as an alternative detergent to branched-alkylbenzene sulfonates (ABS). However, LAS is a petrochemical-based synthetic surfactant made from petroleum feedstocks, n-paraffins, kerosene, and benzene. Although renewable surfactants made from oleochemical feedstock have been developed and are used in household detergents, their capacity is still too low to be utilized in the large market of detergents due to their high cost and low detergency.

Surfactants generally consist of two to three primary components: (1) a hydrophobic group, which is a long-chain alkyl group in the case of LAS, (2) a hydrophilic group, a sulfonate group in the case of LAS, and in some cases (3) a linking molecule, which is benzene in the LAS structure. LAS is commercially made via sulfonation of linear alkylbenzene (LAB) with $SO_3$-air or $SO_3$ in sulfuric acid mixtures. Linear alkylbenzene (LAB), a key monomer of LAS, is industrially produced via alkylation of benzene with alpha-olefins, particularly 1-dodecene, over HF or $AlCl_3$ catalyst. During alkylation of benzene, isomers ranging from 2-phenyl to 6-phenyl LAB are produced except for 1-phenyl LAB due to formation of a carbonium cation on the beta position in alpha-olefins by protonation from acid catalysts. Among the isomers, 2-phenyl LAB is the most biodegradable and exhibits the highest detergency. As a result, a major research focus has been to improve selectivity toward the desired 2-phenyl LAB product and to transition production methods from homogeneous catalysts to solid acid catalysts.

Though selective production of 2-phenyl LAB is desirable, a major drawback of this surfactant is its high Krafft temperature, making it only moderately soluble in hard and cold water. The 2-phenyl isomer exhibits a high packing factor in a crystal lattice due to the terminal-located phenyl group in the straight alkyl chain. This leads to strong interaction between molecules, resulting in a high Krafft temperature. For this reason, 2-phenyl LAB needs a lot of builders, such as, phosphate, sodium carbonate and sodium silicate to increase its solubility; an increase in usage of the builders directly affects the price and efficiency of the detergents.

A solution to address the problem of limited solubility was developed by P&G and UOP in 2001, called modified linear alkylbenzene sulfonate (MLAS). The modified linear alkylbenzene (MLAB) consists of one branched-alkyl group (methyl, ethyl or propyl) on the conventional linear alkylbenzene. MLAS exhibits better solubility compared with commercial LAS due to a lower packing factor by a mono branched-alkyl group. However, MLAS is also prepared by benzene alkylation using a petrochemical-based feedstock of monoalkyl olefins.

Design of new surfactant technologies should preferably be focused on biorenewable technologies for producing surfactant molecules with high biodegradability, strong detergency, and good solubility. Current methods of surfactant production rely on petrochemical-based constituents, such as benzene and long-chain hydrocarbons.

Methods disclosed herein can be utilized as renewable pathways to produce surfactants made from biomass-derived feedstocks, such as furan and lauric acid. Furan is a five-membered aromatic heterocycle that can be produced from the decarbonylation of furfural. Furfural is a biomass-derived chemical, which is produced from the acid-catalyzed dehydration of xylose, a hydrolysis product from the hemicellulosic component of biomass. Lauric acid is a saturated fatty acid, which is produced via the hydrolysis of biomass-derived triglycerides such as palm-kernel oil and coconut oil.

As discussed above, disclosed methods can utilize a selective furan acylation reaction as an alternative to benzene alkylation, for example. Acylation of a furan (as an example only) can be utilized to bond a selected hydrophobic moiety to a furan molecule, which can then be subsequently functionalized with a hydrophilic moiety to form a molecule that can function as a surfactant. Optionally, the acylated furan molecule can be transformed into linear alkylbenzene (LAB) or modified linear alkylbenzene (MLAB) via diels-alder cycloaddition using ethylene gas, for example. The product from the cycloaddition reaction can optionally be subsequently functionalized with a hydrophilic moiety to form a biorenewable drop-in replacement for current methods of LAS or MLAS production.

Acylation reactions contemplated in disclosed methods may be advantageous over alkylation, because acylated aromatic products do not easily isomerize or continue to acylate (e.g. multiple bonding of alkyl chains to an aromatic ring). Conversely, alkylated benzene molecules tend to isomerize, forming products with alkyl branches with variable length, thereby reducing selectivity toward desired products. Additionally, aromatics with terminal linear alkyl substituents can be made by acylation, a product that cannot be produced via alkylation (J. Clayden, N. Greeves, S. Warren, Organic Chemistry $2^{nd}$ Ed., Electrophilic aromatic substitution, Oxford, N.Y., 2012, pp. 493-494). An existing technology which also forms a furan aromatic as part of the surfactant, as developed by Procter & Gamble, utilizes a less-selective and more costly Grignard reaction instead of acylation in order to combine an aromatic furan, such as furfural, with a hydrophobic alkyl chain (United States Patent Pub. No. 2015/0150768, the disclosure of which is incorporated herein by reference thereto).

In some embodiments, furan acylation with lauric acid can be performed by aid of trifluoroacetic anhydride (TFAA), which is an acylating agent for producing lauric anhydride. As shown in Scheme 1, TFAA can be subsequently regenerated from TFA using phosphorous pentoxide (J. M. Tedder, Chem. Rev. 1955, 55 (5), 787-827; and T. P. Smyth, B. W. Corby, J. Org. Chem. 1998, 63, 8946-8951). By this recyclable reaction, molecules to be used for furan acylation, including but not limited to 2-dodecanoylfuran (DOF) and 2-furyl dodecyl ketone, can be prepared.

Scheme 1. Tandem anhydride and acylation of fatty acid over trifluoroacetic anhydride.

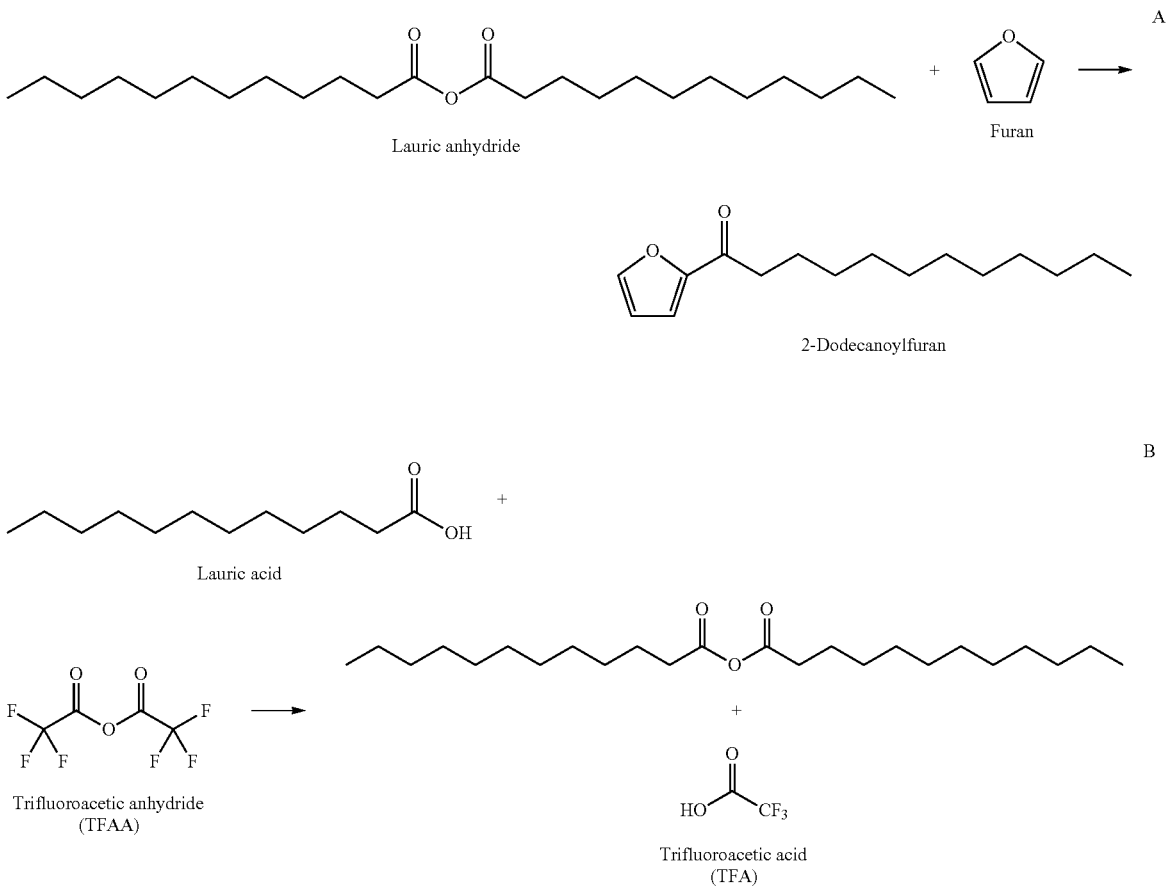

-continued

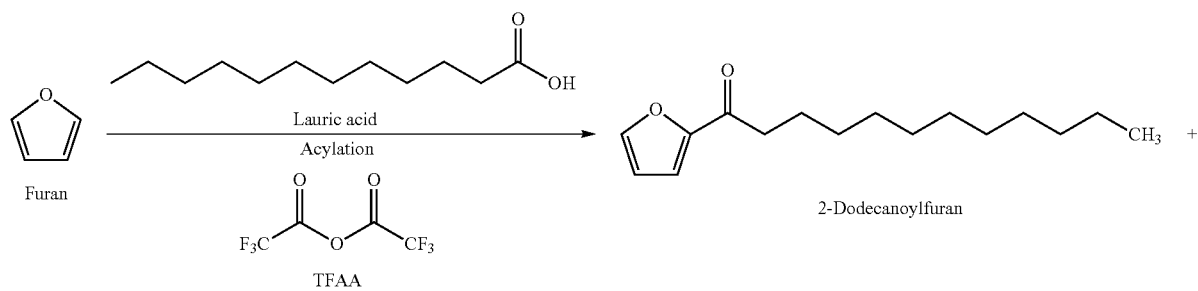

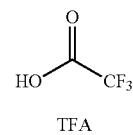

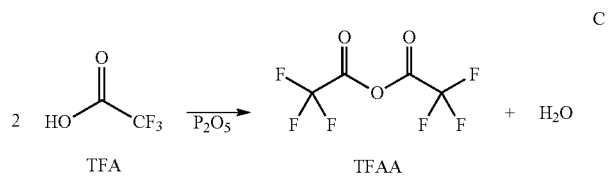

As seen in Scheme 2, 2-dodecanoylfuran or other acylated furans can be used to synthesize various types of renewable surfactants. The ketone group can be removed by the hydrogenation over a metal catalyst such as a copper-based catalyst, forming an alkylfuran such as 2-dodecylfuran (DF).

Scheme 2. Proposed pathways for renewable surfactants from furan and fatty acids. Presented pathways represent one of many possible permutations in the order in which the reactions are carried out.

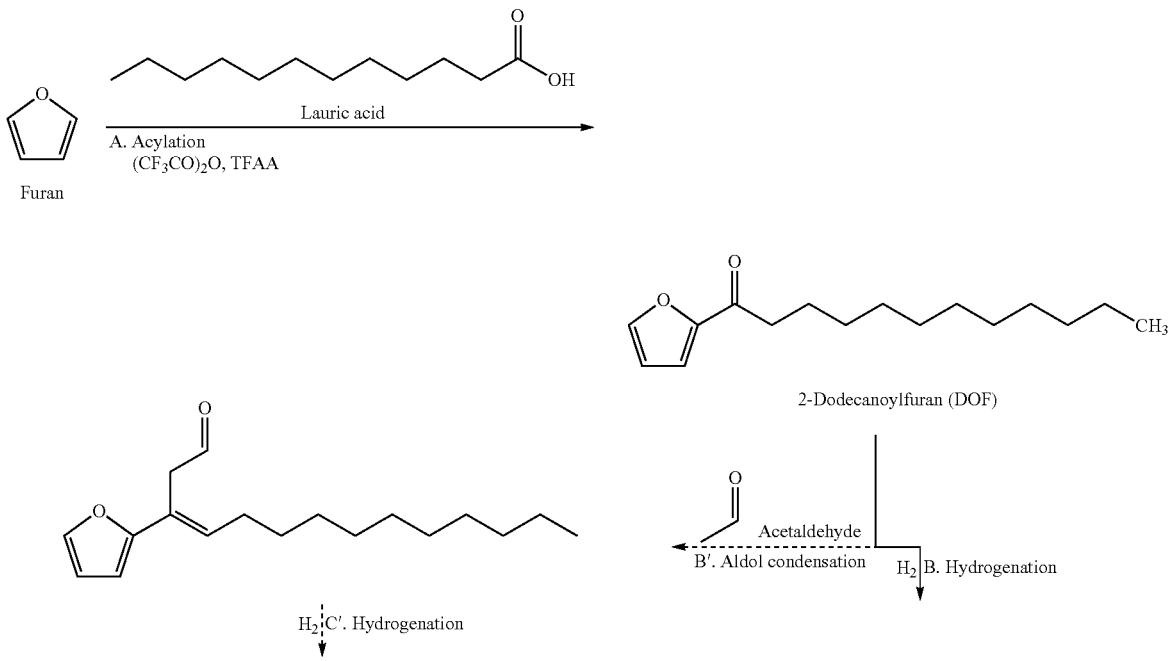

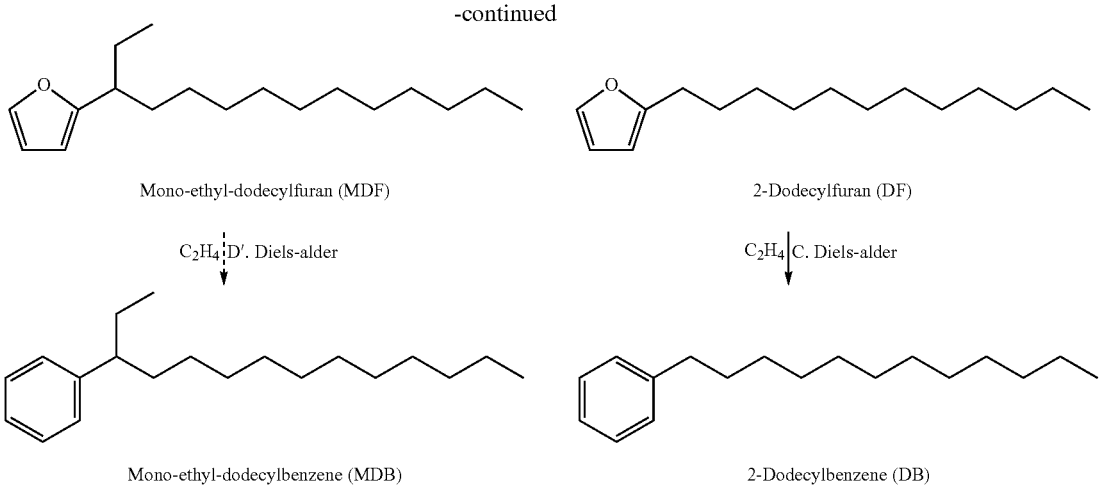

Mono-ethyl-dodecylfuran (MDF)  |  2-Dodecylfuran (DF)

Mono-ethyl-dodecylbenzene (MDB)  |  2-Dodecylbenzene (DB)

The alkylfuran molecule can be used in one of two ways: (1) cycloaddition of alkylfuran to form alkylbenzene, which can then be subsequently functionalized with a hydrophilic moiety, such as a sulfonate in the case of LAS, or (2) direct functionalization of the alkylfuran with a hydrophilic moiety to form a furan-based surfactant for example.

Recently, attempts have been made toward developing a furan-based surfactant (A. Gassama, Cédric Ernenwein, A. Youssef, M. Agach, E. Riguet, S. Marinković, B. Estrine, N. Hoffmann, Green Chem. 2013, 15, 1558-1566; US Patent Pub. No. 2015/0150768 A 1; and G. A. Kraus, J. J. Lee, J. Surfact. Deterg. 2013, 16, 317-320). Furan-based surfactants have more hydrophilicity and solubility than benzene due to the oxygen atom in aromatic ring. Environmentally, furan is safe to use for household detergents, but benzene is classified as toxic and a carcinogen in the human body.

In order to form a benzene-based surfactant such as LAS, the alkylfuran molecule such as 2-dodecylfuran can be converted to an alkylbenzene such as dodecylbenzene (1-phenyl LAB) through the cycloaddition with ethylene over a solid acid such as zeolite catalyst, for example. Cycloaddition of five-membered aromatics to make six-membered aromatics has been demonstrated using high pressure and high temperature reactors (C.-C. Chang, S. K. Green, C. L. Williams, P. J. Dauenhauer, W. Fan, Green Chem. 2014, 16, 585-588; and S. K. Green, R. E. Patet, N. Nikbin, C. L. Williams, C.-C. Chang, J. Yu, R. J. Gorte, S. Caratzoulas, W. Fan, D. G. Vlachos, P. J. Dauenhauer, Appl. Catal. B 2015, 180, 487-496).

As mentioned above, the 1-phenyl LAB-based surfactant has poor solubility despite its enhanced biodegradability and detergency. Alternatives to 1-phenyl LAS incorporate a side chain in order to improve solubility. In order to produce such a modified alkylfuran or alkylbenzene an aldol-condensation, for example, of DOF with acetaldehyde or other aldehyde-containing hydrocarbon can be utilized. Base-catalyzed aldol condensation forms a carbon-carbon bond between the ketone and aldehyde group (T. Tago, H. Konno, S. Ikeda, S. Yamazaki, W. Ninomiya, Y. Nakasaka, T. Masuda, Catal. Today 2011, 164, 158-162; R. Mestres, Green Chem. 2004, 6, 583-603: and L. Faba, E. Diaz, S. Ordo~nez, Appl. Catal. B 2012, 113-114, 201-211).

As a result, of such specific, illustrative method steps, mono-ethyl dodecylfuran (MDF) can be produced by sequential reactions of aldol addition and hydrogenation of 2-dodecanoylfuran. Finally, the modified (mono-ethyl) LAB could be made by cycloaddition of MDF.

The present disclosure is illustrated by the following examples. It is to be understood that the particular examples, assumptions, modeling, and procedures are to be interpreted broadly in accordance with the scope and spirit of the disclosure as set forth herein.

Examples

Disclosed herein are methods of making compounds that can illustratively include aromatic-based surfactants that include a hydrophilic moiety, a hydrophobic group, and an aromatic group, where, the hydrophilic group can be anionic, cationic, nonionic, or zwitterionic and the hydrophobic group can be a linear or branched, saturated, or unsaturated hydrocarbon chain. The compounds can be represented by formula I:

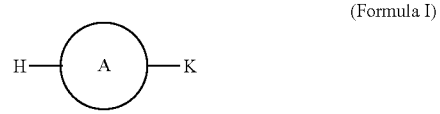

(Formula I)

wherein, A is the aromatic moiety, H, is the hydrophobic moiety and K is the hydrophilic moiety. Illustrative possible aromatic groups A can include but are not limited to those in Table 1. Illustrative possible hydrophilic moieties, K can in the case of ionic (anionic and cationic) surfactants, include the surface active ion and a counter metal ion which can include but are not limited to those in Table 2. Illustrative possible hydrophobic moieties, H can include but are not limited to alkyl chains between 6 and 26 carbons that may be linear, branched, cyclic or any combination thereof and may be saturated or unsaturated.

Formation of the compounds can be achieved in numerous permutations of reaction orders as well as reaction conditions, such as temperature, pressure, reactant, and catalyst type, and combinations thereof. In some illustrative embodiments, methods can include four main steps or chemical reactions: acylation, hydrogenation, aldol condensation, and functionalization with a hydrophilic group, which can be performed in any order or simultaneously with any other reaction. Specifically, reactions such as the aldol condensation and sulfonation can be carried out at any point during the overall process, yielding a number of permutations in chemical reaction order. An example of one of these permutations is shown in Scheme 3, in which the 2-dodecylfuran molecule can be functionalized with a hydrophilic group before or after cycloaddition to form a benzene aromatic ring. In the case of these permutations, aldol condensation could also be performed at any step in the process.

Scheme 3. An example of one of the permutations of the order in which reactions are carried out shows functionalization with a hydrophilic group (K) can occur either before or after cycloaddition.

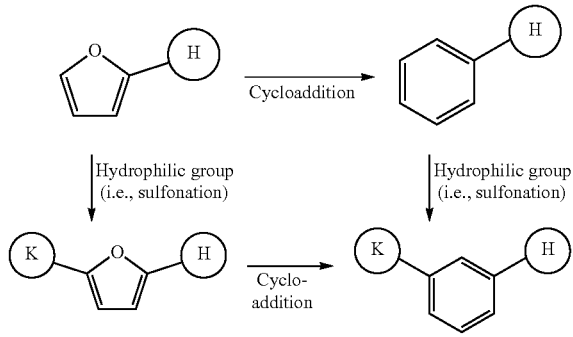

Additionally, each reaction presented can be carried out using a selection of acid, base, or metal catalysts (specific examples of which are illustrated in Table 2 above), which can be homogeneous, heterogeneous, or otherwise supported, or any combination of multiple catalysts. Reactions can also be carried out heterogeneously or homogeneously in the gas, liquid, or solid phases or any combination of phases or supercritical conditions.

Acylation Reaction to Form 2-Dodecanoylfuran, Hydrogenation Reaction to Form 2-Dodecylfuran, and Sulfonation to Form Sodium 2-Dodecylfuran-5-Sulfonate.

Hexane (95%), Furan (99%), and Trifluoroacetic anhydride (99%) were purchased from Sigma-Aldrich. Lauric acid (99%) was purchased from Acros, and n-tridecane (98%) was from Alfa Aesar. 2-dodecylfuran (95%) was purchased from MP Biomedical. H-BEA catalyst (CP814E, Si/Al=12.5) and copper chromite catalyst were obtained from Zeolyst and Sigma-Aldrich, respectively. H-BEA was calcined at 550° C. for 12 hr with a ramping rate of 1° C. min$^{-1}$ in a tube furnace under air flow. The reduction of copper chromite was carried out at 300° C. for 3 hr under 10% $H_2$/Argon flow.

Batch reactions for production of 2-dodecanoylfuran (DOF) were conducted in a 100 mL high pressure Parr Reactor. In a typical reaction, the Furan (1.0 mL, 0.014 mols), lauric acid (4.0 mL, 0.018 mols), trifluoroacetic anhydride (2.0 mL, 0.014 mols) and n-tridecane (internal standard, 0.5 mL, 0.002 mols) were dissolved in hexane (10 mL), and 0.2 g of the H-BEA catalyst was introduced to the mixture. The sealed reactor was purged with $N_2$ twice to remove the residual air in the reactor. The reactor was then heated to the reaction temperature (room temperature or 50-180° C.) under vigorous stirring (1,000 rpm). The reactor was subsequently pressurized to 200 psi (at desired temperature) with $N_2$ to keep liquid phase of the reactants. After reaction for a desired reaction time, the reactor was cooled to room temperature and the gases were vented. The products were identified by a GC-MS (Agilent 7890A connected with Triple-Axis MS detector, Agilent 5975C) and quantified by a GC (Agilent 7890A) equipped with an HP-5 column and a flame ionization detector. The selectivity of the 2-dodecanoylfuran was calculated to the produced moles of DOF over the reacted moles of the furans. The response factor of the DOF was determined by the QCD method (S. Maduskar, A. R. Teixeira, A. D. Paulsen, C. Krumm, T. J. Mountziaris, W. Fan, P. J. Dauenhauer, Lab Chip 2015, 15, 440-447), because the standard chemical of 2-dodecanoylfuran was not supplied commercially.

Hydrogenation of 2-dodecanoylfuran to make 2-dodecylfuran (DF) was carried out in a 100 mL Parr reactor. The prepared 2-dodecanoylfuran (2.0 mL, 0.0077 mols) and n-tridecane (internal standard, 0.5 mL, 0.002 mols) were dissolved in hexane (30 mL), and 0.5 g of copper chromite catalyst was introduced to the mixture. The reactor was pressurized with hydrogen in a range of 100-350 psi at the desired reaction temperature (180-220° C.). The selectivity of the 2-dodecylfuran was calculated to the produced moles of DF over the reacted moles of the DOF. [90] The desired products (DOF and DF) were concentrated by rotary evaporator (Hei-VAP/G5, Heidolph) with liquid nitrogen in the condenser. Several batch reactions were conducted without the internal standard chemical (n-tridecane) to collect the product solutions. The rotary evaporator was operated at room temperature for 30 min under high vacuum to remove the light molecules (hexane, furan, TFAA and TFA). Afterwards, the remaining solution was further concentrated at 70° C. for 2 hr under high vacuum.

2-dodecylfuran was sulfonated and neutralized to make sodium 2-dodecylfuran-5-sulfonate by three different methods as follows. Method 1: 2-dodecylfuran (5.9 g, 25 mmol) was dissolved in isopropanol (100 mL), and the solution was added to a solution of $NaHSO_3$ (5.2 g, 50 mmol) in water (75 mL). The mixture was stirred at 50° C. for 28 hr (A. Gassama, Cedric Ernenwein, A. Youssef, M. Agach, E. Riguet, S. Marinković, B. Estrine, N. Hoffmann, Green Chem. 2013, 15, 1558-1566). Method 2: 2-dodecylfuran (5.9 g, 25 mmol) was added to a slurry of sulfur trioxide-pyridine complex (4 g, 25 mmol) in 1,2-dichloroethane (25 mL), and the mixture stirred at room temperature for 3 days. After then, warm water (75 mL) was introduced to the slurry. The aqueous phase was controlled to a pH 7.5 using sodium carbonate and then evaporated to crystalline phase (J. F. Scully, E. V. Brown, J. Org. Chem. 1954, 19(6), 894-901; and G. Trummlitz, E. Seeger, W. Engel (Boehringer Ingelheim GmbH, Germany), 4,5-Dimethyl-Thieno [3,2-d] Iso-Thiazolo-3(2H)-One-1,1-Dioxides, Compositions, And Methods Of Use As A Sweetener, U.S. Pat. No. 4,233,333, Nov. 11, 1980). Method 3: 2-dodecylfuran (5.9 g, 25 mmol) was added to a slurry of sulfur trioxide-pyridine complex (5.7 g, 36 mmol) in acetonitrile (20 mL). The mixture was heated at 40° C. and stirred under nitrogen atmosphere. After 24 hr, the slurry was added to a solution of NaOMe/MeOH (7.8 g, 36 mmol) in methanol (20 mL). The solvent was evaporated overnight, and the residue mixture was added to warm water (70° C.). The mixture was placed in a refrigerator for 2.0 hr, and the crystalline phase was collected by filtration (US Pat. Pub. No. 2015/0150768).

The produced 2-dodecanoylfuran (DOF), 2-dodecylfuran (DF) and sodium dodecylfuran sulfonate (SDFS) were analyzed by $^1$H NMR spectroscopy (Bruker AX400, 400 MHz). The $^1$H NMR of the products were dissolved in $CDCl_3$ solutions containing with a 5 mM of tetramethylsilane (TMS) as an internal standard.

Surface tension and critical micelle concentration (CMC) of the surfactants were measured by Du Noüy ring method using a surface tensiometer. Krafft point (Tx) of the surfactants was measured by estimating the degree of counterion dissociation using conductivity meter (COND 6+, Oakton/Eutech Instruments). An aqueous solution of surfactant concentrated to a CMC value was prepared and placed in a refrigerator for 4.0 hr. The solution was heated to 30-40° C. from 5-6° C. with a ramping rate of 0.5° C. min$^{-1}$ under vigorous stirring (J. Z. Manojlović, Thermal Science 2012, 16, S631-S640; and C. Vautier-Giongo, B. L. Bales, J. Phys. Chem. B 2003, 107, 5398-5403).

Results

The acylation of furan with lauric acid was carried out at room temperature (r.t.) to 180° C. for 6.0 hr in hexane and THF solvents with trifluoroacetic anhydride. As seen in Table 5, the conversion of furan and lauric acid (LA) were 100% in a range of temperature from r.t. to 100° C.

TABLE 5

Summarized results for the acylation of furan with lauric acid and trifluoroacetic anhydride.

| Conditions | Furan conversion (%) | Lauric acid conversion (%) | TFAA conversion (%) | 2-dodecanoyl selectivity (%) |
|---|---|---|---|---|
| 25° C. | 100 | 100 | 51.1 | 87.0 |
| 25° C. | 100 | 100 | 71.6 | 81.3 |
| 50° C. | 100 | 100 | 70.2 | 75.6 |
| 100° C. | 100 | 100 | 27.4 | 27.4 |
| 150° C. | 100 | 95.6 | 100 | 43.9 |
| 180° C. | 100 | 78.3 | 100 | 13.5 |
| 150° C. | 53.9 | 91.2 | 100 | 20.1 |

*Reaction Conditions: 200 psi (N$_2$), 0.014 mols of Furan, 0.018 mols of lauric acid, and 0.028 mols of TFAA in hexane (10 mL), HBEA 0.2 g, 6 hrs.

Figure 1B:
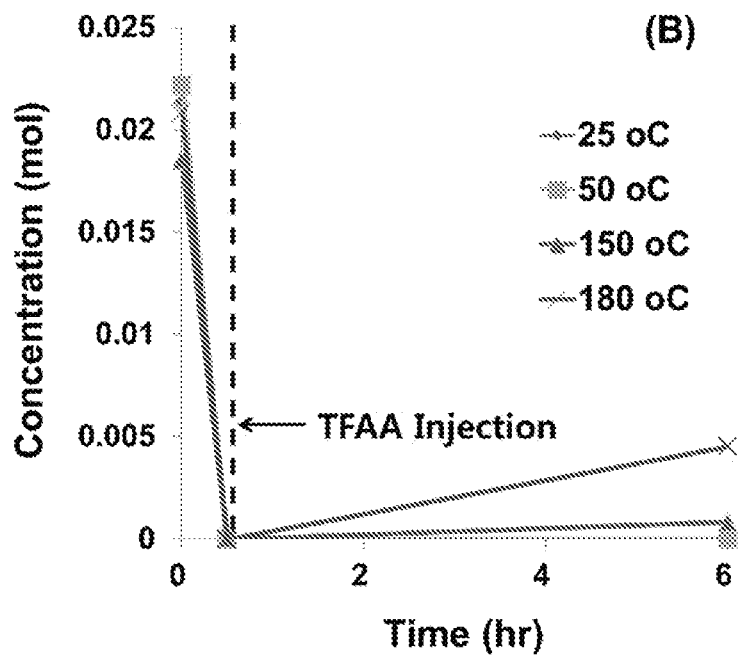
Figure 2:
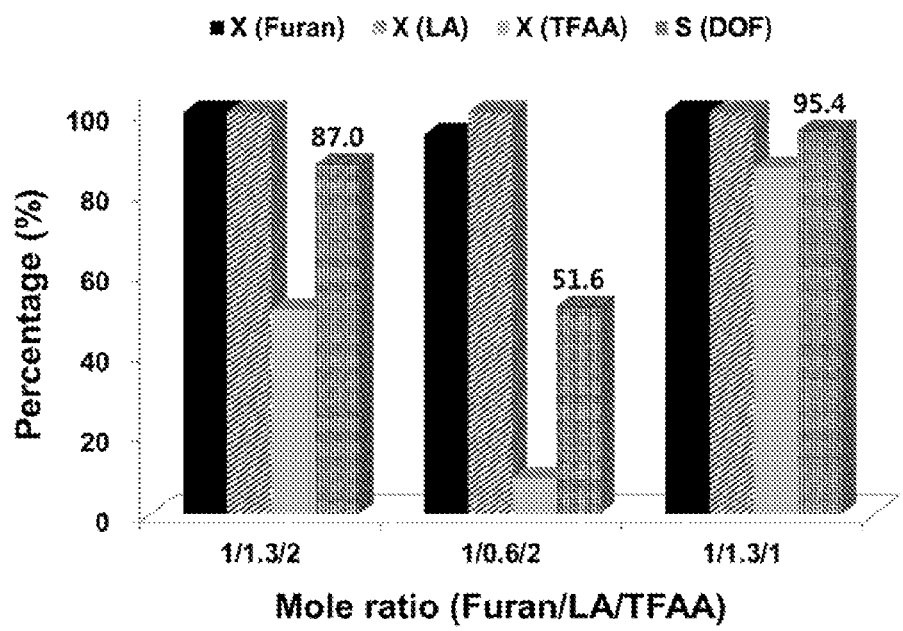
FIG. 2 shows results for the acylation of furan and lauric acid with different mole ratios of reactants (Mole ratio (1/1.3/1): 0.014 moles of Furan/0.018 moles of lauric acid/ 0.014 moles of TFAA, Reaction conditions: Room temperature, 1 atm, no catalysts).
Figure 3:
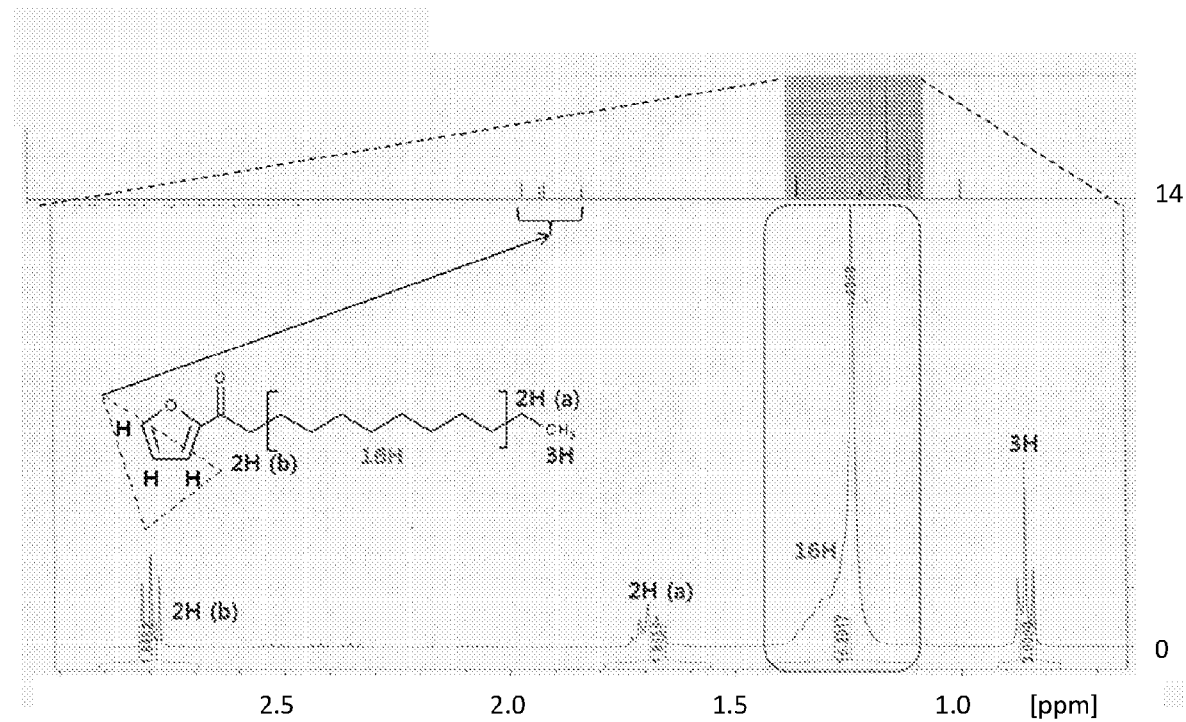
FIG. 3 shows the 1H NMR spectrum of purified and concentrated 2-dodecanoylfuran after acylation.

Above 150° C., the lauric acid (LA) conversion slightly decreased. With decreasing reaction temperature, the selectivity of 2-dodecanoylfuran (DOF) sharply increased up to 87% at room temperature without the H-BEA catalyst. In the use of THF solvent, acylation was not observed due to high reactivity of THF with trifluoroacetic anhydride. The selectivity to DOF was lower at high reaction temperatures, because acylation is a reversible reaction in the presence of trifluoroacetic anhydride. The data in FIGS. 1A and 1B show the change of concentration of 2-dodecanoylfuran (FIG. 1A) and lauric acid (FIG. 1B), respectively, during a reaction. After addition of the trifluoroacetic anhydride, DOF was rapidly produced with about 90-95% selectivity within a few minutes. However, the produced DOF gradually decreases with continued reaction. The decreasing rate of selectivity was faster at high temperatures. Above 150° C., conversion of lauric acid was reversed. We investigated the effect of mole ratio of reactants to production of DOF (FIG. 2). With a decrease the lauric acid concentration, the TFAA conversion and the selectivity of the DOF decreased. However, with an equimolar ratio of the furan and TFAA, the DOF selectivity increased to 95%, and the TFAA conversion also increased. Therefore, the reaction condition of the furan acylation with lauric acid under TFAA was carried out at room temperature, no catalyst, and the equimolar ratio of furan and TFAA. The 2-dodecanoylfuran, furyl lauryl ketone, prepared by acylation was identified by $^1$H NMR. As seen in FIG. 3, the broad multiply peak (chemical shift: 1.24~1.38 ppm) was calculated for the sixteen protons. Therefore, the produced furyl ethyl ketones were confirmed to consist of furyl-2-(C$_{12}$ alkyl)-ketone, 2-dodecanoylfuran. ($^1$H NMR (400 MHz, CDCl$_3$): δ 0.84-0.87 (m, 3H), 1.24-1.38 (brm, 16H), 1.66-1.73 (m, 2H), 2.78-2.82 (m, 2H), 6.50-6.52 (m, 1H), 7.17-7.18 (m, 1H), 7.56 (m, 1H)) The 2-dodecanoylfuran was also identified by GC-MS. (GC MS (EI) m\z (relative intensity): 151 (3.4), 123 (20.1), 111 (10.9), 110 (99.9), 95 (31.6), 81 (2.6), 55 (5.5), 43 (4.4), 41 (6.2), 39 (3.6)).

Figure 4A:
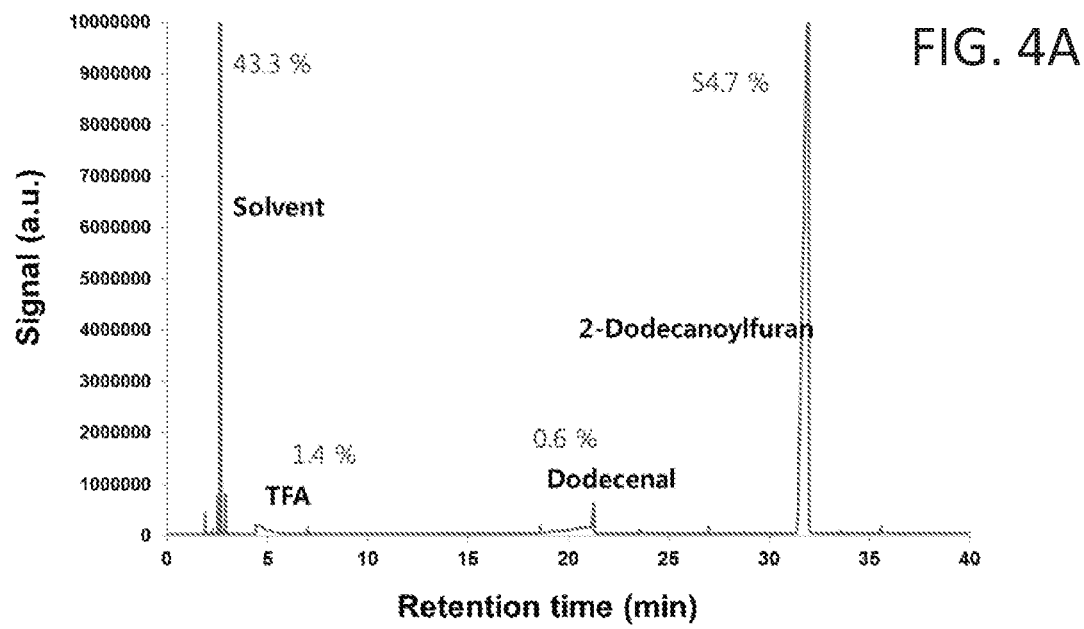
FIGS. 4A and 4B show typical GC profiles of product mixtures after acylation (FIG. 4A) and 2-dodecanoylfuran concentrated with rotary evaporator (FIG. 4B).
Figure 4B:
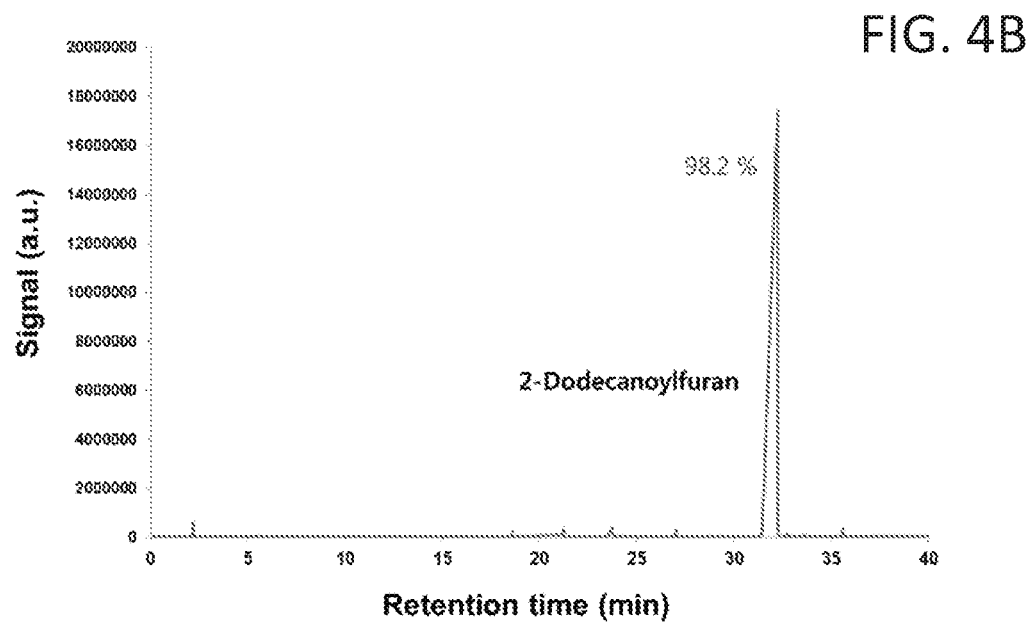

The acylation was carried out without an internal standard (n-tridecane) in several batches and the products were collected in order to use the 2-dodecanoylfuran as a reactant in hydrogenation (FIG. 4A shows the GC profile of the product mixtures after acylation). Concentrated 2-dodecanoylfuran was obtained with 98% purity using a rotary evaporator (FIG. 4B shows the GC profile of product mixtures after purification). The hydrogenation of 2-dodecanoylfuran was performed at 220° C. over copper chromite in various hydrogen pressures. The possible reaction scheme in hydrogenation of DOF over copper chromite is shown in Scheme 4.

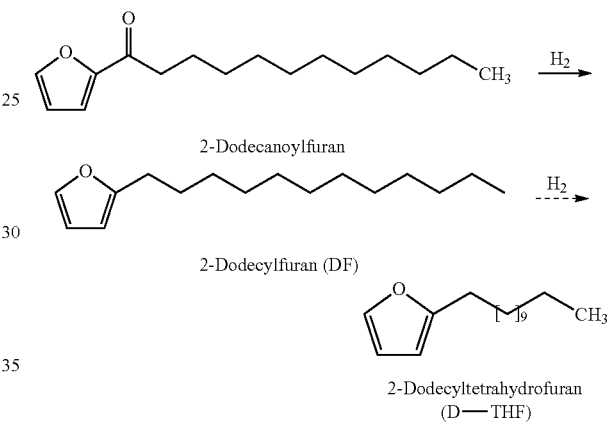

Scheme 4. Liquid-phase hydrogenation of 2-dodecanoylfuran over copper chromite.

At first, a ketone group of DOF was removed by hydrogenation, resulting in production of 2-dodecylfuran (DF) as a desired product. However, 2-dodecyl-tetrahydrofuran (D-THF) can also be made by further hydrogenation of DF as a main side product. As shown in Table 6, when the reduced copper chromite was used for the catalyst, more amount of D-THF was produced than DF.

TABLE 6

Summarized results for the hydrogenation of 2-dodecanoylfuran.

| Conditions | 2-dodecanoylfuran conversion (%) | 2-dodecylfuran selectivity (%) | 2-dodecyl-tetrahydrofuran selectivity (%) | Unknown selectivity (%) |
|---|---|---|---|---|
| 100 psi | 100 | 91.6 | 7.3 | 1.1 |
| 150 psi | 100 | 59.5 | 12.3 | 28.2 |
| 250 psi | 100 | 54.8 | 18.3 | 26.9 |
| 350 psi | 100 | 0.9 | 47.6 | 51.5 |
| 250 psi (Reduced CuCr) | 99.6 | 18.3 | 74.9 | 6.9 |

*Reaction Conditions: 220° C., pressures of H$_2$ (at 220° C.), 0.0077 mols of 2-dodecanoylfuran in hexane (30 mL), copper chromite 0.5 g, 5 hrs Non-reduced copper chromite was a more selective catalyst for producing 2-dodecfylfuran (DF). The selectivity of DF was enhanced with decreasing pressure of hydrogen, reaching up to 91% in 100 psi of H$_2$. On the other hand, the selectivity to D-THF increased at 350 psi of H$_2$. In both the high and low-pressure system, the conversion of DOF approached 100%. However, the selectivity to DF decreased after 3.0 hr in 350 psi of $H_2$, and the consumed 2-dodecylfuran was increasingly converted to D-THF by further hydrogenation of the furan ring (FIGS. 5A and 5B).

Figure 6:
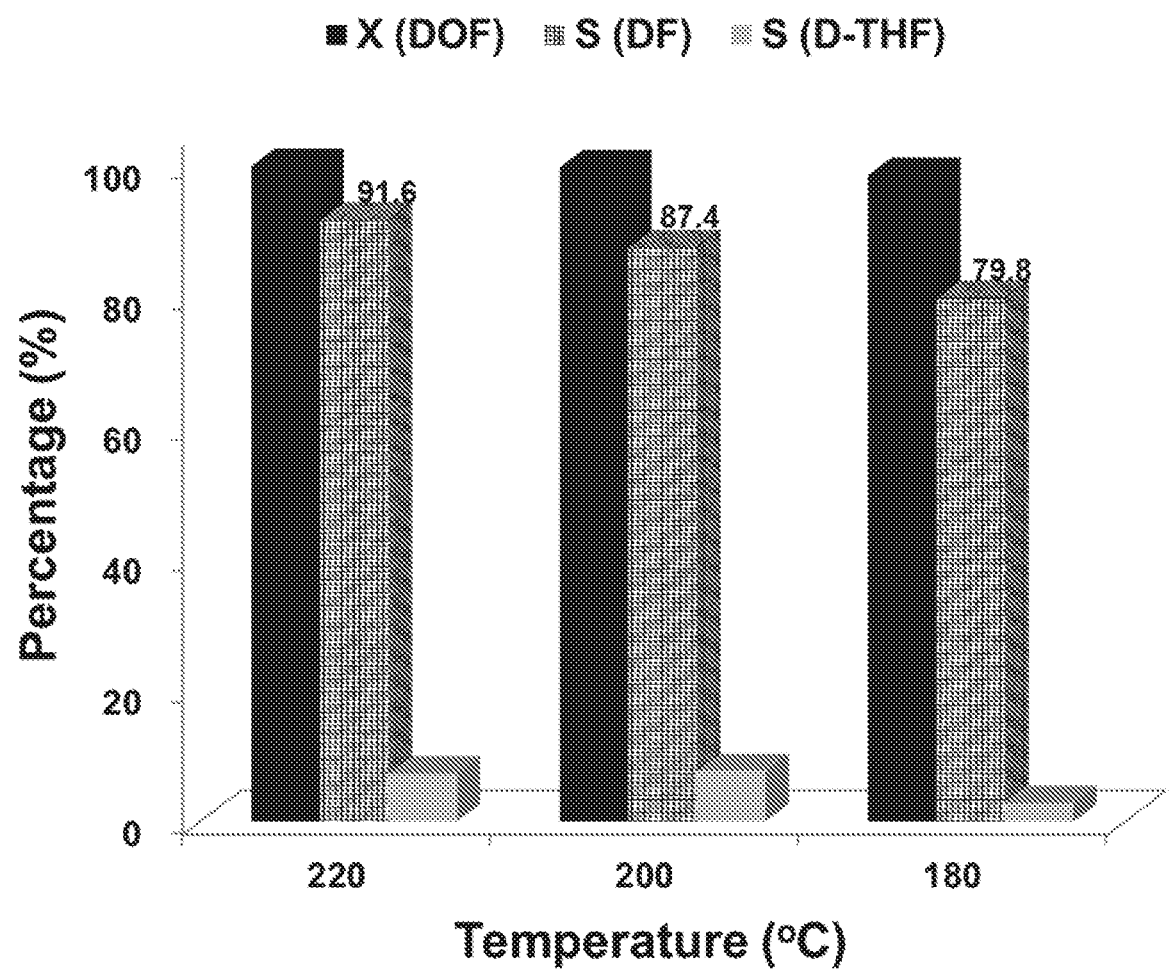
FIG. 6 shows results for the hydrogenation of 2-dodecanoylfuran at 180-220° C. in 100 psi of $H_2$ (Reaction Conditions: 100 psi of $H_2$ (at reaction temperature), 0.0077 mols of 2-dodecanoylfuran in hexane (30 mL), copper chromite 0.5 g, 5 hrs).
Figure 7:
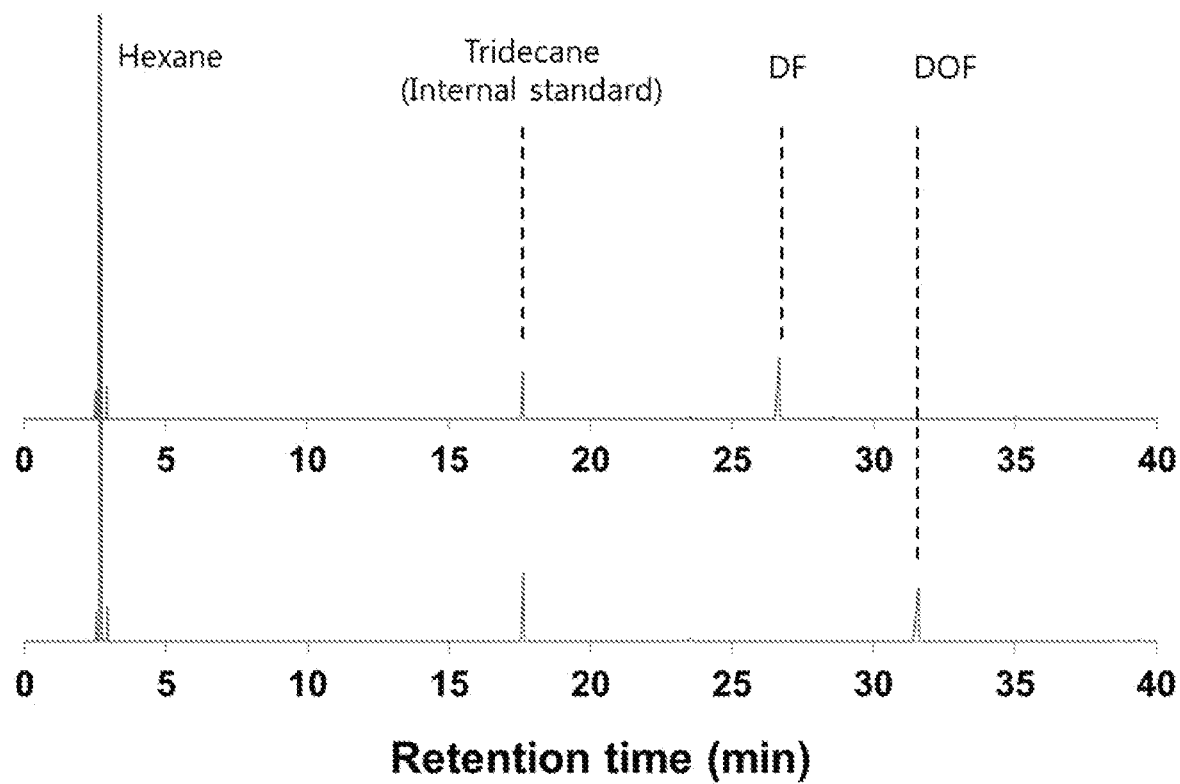
FIG. 7 shows typical GC chromatograms of reactant mixtures (bottom trace) and the products after hydrogenation of 2-dodecanoylfuran (top trace).

The optimum temperature to maximize the selectivity toward production of DF was also investigated. Interestingly, when the temperature was lowered from 220 to 180° C., the selectivity to DF and D-THF also decreased (FIG. 6). To improve selectivity toward 2-dodecylfuran via removal of the ketone from 2-dodecanoylfuran, temperatures above 220° C. are required in addition to moderate hydrogen pressure below 100 psi to prevent hydrogenation of the furan rings. Comparison of the gas chromatograms of the reactant sample (bottom trace) with the products after 5 hrs of reaction (top trace) is represented in FIG. 7, and the desired product, 2-dodecylfuran was identified by GC-MS. (GC MS (EI) m\z (relative intensity): 236 (17.7), 123 (17.6), 96 (12.1), 95 (58.3), 94 (13.5), 82 (42.6), 81 (99.9), 53 (10.1), 43 (10.2), 41 (12.3)).

Thus, embodiments of methods of forming aromatic containing compounds are disclosed. The implementations described above and other implementations are within the scope of the following claims. One skilled in the art will appreciate that the present disclosure can be practiced with embodiments other than those disclosed. The disclosed embodiments are presented for purposes of illustration and not limitation.

What is claimed is:

1. A method comprising:
   acylating a furan containing compound by reacting the furan containing compound with an anhydride containing compound comprising a six (6) to 26 carbon alkyl chain to form an acylated furan containing compound.

2. The method according to claim 1 further comprising subjecting the acylated furan compound to hydrogenation to replace the ketone functionality with a methylene.

3. The method according to claim 1 further comprising functionalizing the acylated furan containing compound with a hydrophilic moiety.

4. The method according to claim 3, wherein the functionalization occurs via sulfonation.

5. The method according to claim 1 further comprising subjecting the acylated furan containing compound to a cycloaddition reaction.

6. The method according to claim 5, wherein the cycloaddition is a diels-alder reaction.

7. The method according to claim 6, wherein the cycloaddition occurs by reacting the acylated furan containing compound with ethylene ($C_2H_4$).

8. The method according to claim 1 further comprising adding an alkyl group to the group added via acylation of the furan containing compound.

9. The method according to claim 8, wherein the alkyl group is added to the group added via acylation before hydrogenation to replace the ketone group with a methylene group.

10. The method according to claim 9, wherein adding the alkyl group to the group added via acylation is done by an aldol-condensation.

11. The method according to claim 3, wherein the functionalization of the acylated furan containing compound occurs after hydrogenation of the acylated aromatic compound, or before hydrogenation of the acylated aromatic compound.

12. The method according to claim 5, wherein the cycloaddition occurs after hydrogenation of the acylated furan compound, or before hydrogenation of the acylated aromatic compound.

13. The method according to claim 5, wherein the cycloaddition occurs after functionalization of the acylated furan compound, or before functionalization of the acylated aromatic compound.

14. The method according to claim 1, wherein the acylated furan containing compound has previously been functionalized with a hydrophilic moiety.

15. The method according to claim 1, wherein the anhydride that acylates the furan containing compound is formed by reacting a fatty acid and a precursor anhydride.

16. The method according to claim 15, wherein the reaction of the fatty acid and the precursor anhydride takes place in the same reaction vessel as does the acylation of the furan containing compound.

17. A method comprising:
   acylating a furan containing compound by reacting the furan containing compound with an anhydride containing compound comprising a six (6) to 26 carbon alkyl chain to form an acylated furan containing compound;
   subjecting the acylated furan containing compound to a cycloaddition reaction;
   adding an alkyl group to the group added via acylation of the furan containing compound;
   hydrogenating the acylated compound to replace a ketone group with a methylene group; and
   functionalizing the acylated aromatic containing compound with a hydrophilic moiety.

18. The method according to claim 17, wherein the anhydride that acylates the furan containing compound is formed by reacting a fatty acid and a precursor anhydride.

19. The method according to claim 18, wherein the reaction of the fatty acid and the precursor anhydride takes place in the same reaction vessel as does the acylation of the furan containing compound.

20. The method according to claim 1, wherein the furan containing compound is

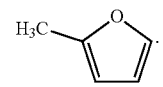

.

* * * * *